United States Patent
Himori et al.

(10) Patent No.: US 12,065,521 B2
(45) Date of Patent: Aug. 20, 2024

(54) COMPOUND HAVING POLYCYCLIC AROMATIC SKELETON, AND ENDOPEROXIDE COMPOUND OF SAME

(71) Applicants: Kawasaki Kasei Chemicals Ltd., Kawasaki (JP); National University Corporation YOKOHAMA National University, Yokohama (JP)

(72) Inventors: Shunichi Himori, Kawasaki (JP); Keita Iuchi, Kawasaki (JP); Akihiko Yamada, Kawasaki (JP); Hiroaki Gotoh, Yokohama (JP); Kazuhisa Sakakibara, Yokohama (JP)

(73) Assignees: Kawasaki Kasei Chemicals Ltd., Kawasaki (JP); National University Corporation YOKOHAMA National University, Yokohama (JP)

( * ) Notice: Subject to any disclaimer, the term of this patent is extended or adjusted under 35 U.S.C. 154(b) by 277 days.

(21) Appl. No.: 17/427,850

(22) PCT Filed: Feb. 12, 2019

(86) PCT No.: PCT/JP2019/004912
§ 371 (c)(1),
(2) Date: Aug. 2, 2021

(87) PCT Pub. No.: WO2019/159908
PCT Pub. Date: Aug. 22, 2019

(65) Prior Publication Data
US 2022/0127385 A1  Apr. 28, 2022

(30) Foreign Application Priority Data
Feb. 13, 2018 (JP) .................... 2018-023575

(51) Int. Cl.
*C08F 2/50* (2006.01)
*C08K 5/14* (2006.01)

(52) U.S. Cl.
CPC ................ *C08F 2/50* (2013.01); *C08K 5/14* (2013.01)

(58) Field of Classification Search
CPC ...... C08F 2/42; C08F 2/48; C08F 2/50; C08F 4/34; C08K 5/14; C07D 319/02; C07D 493/08
See application file for complete search history.

(56) References Cited

U.S. PATENT DOCUMENTS

| | | | | |
|---|---|---|---|---|
| 4,563,413 A * | 1/1986 | Messer | ........... | G03F 7/031 430/920 |
| 10,570,227 B2 * | 2/2020 | Numata | ........... | C08F 222/10 |
| 11,149,103 B2 * | 10/2021 | Numata | ........... | C08F 222/102 |

FOREIGN PATENT DOCUMENTS

| | | |
|---|---|---|
| CN | 105037587 A | 11/2015 |
| CN | 113166036 | 7/2021 |
| JP | H 06-50397 B2 | 6/1994 |
| JP | 2003-206319 A | 7/2003 |
| JP | 2003-261572 A | 9/2003 |
| JP | 2004-277660 A | 10/2004 |
| JP | 2007-118396 A | 5/2007 |
| JP | 2008-221159 A | 9/2008 |
| JP | 2011-42743 A | 3/2011 |
| JP | 2011-236297 A | 11/2011 |
| JP | 2011-246606 A | 12/2011 |
| JP | 2012-51 4079 A | 6/2012 |
| JP | 2015-105292 A | 6/2015 |
| JP | 2015-183139 A | 10/2015 |

(Continued)

OTHER PUBLICATIONS

International Search Report dated Apr. 16, 2019 in PCT/JP2019/004912 filed on Feb. 12, 2019, 2 pages.
Kakeya et al., "Formation of Anthracene Cation Radicals from 9,10-Dihydro-9,10-epidioxyanthracene Derivatives; Peroxide—initiated Cationic Polymerization of Styrene in Liquid Sulphur Dioxide", J.C. S. Perkin I, 1976, vol. 1, pp. 87-90.
Bauch et al., "Intermediates in the cleavage of endoperoxides", Journal of Physical Organic Chemistry, 2017, vol. 30, e3607, 6 total pages.

(Continued)

*Primary Examiner* — Sanza L. McClendon
(74) *Attorney, Agent, or Firm* — Oblon, McClelland, Maier & Neustadt, L.L.P.

(57) ABSTRACT

A radical polymerization method may use a compound having a polycyclic aromatic skeleton and an endoperoxide compound having a polycyclic aromatic skeleton. An endoperoxide compound may have a polycyclic aromatic skeleton of formula (1), and a compound may have a polycyclic aromatic skeleton, which is a raw material of the endoperoxide compound:

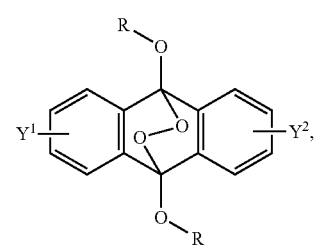

(1)

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group.

11 Claims, 1 Drawing Sheet

(56) References Cited

FOREIGN PATENT DOCUMENTS

| JP | 2015183139 A | * | 10/2015 |
| JP | 2016-84447 A | | 5/2016 |
| JP | 2017-57249 A | | 3/2017 |
| WO | WO 2017/177795 A1 | | 10/2017 |
| WO | WO 2017/177796 A1 | | 10/2017 |

OTHER PUBLICATIONS

Odian, Principles of Polymerization, Fourth Edition, 2004, pp. 254-256.
Matsumoto et al., "Organic Syntheses by the Use of Singlet Oxygen", Journal of Synthetic Organic Chemistry, 1977, vol. 35, No. 3, pp. 188-200 (with English Abstract).
Balta et al., "Thioxanthone-Diphenyl Anthracene: Visible Light Photoinitiator", Macromolecules, 2012, vol. 45, pp. 119-125 (with cover sheet).
Kiriyama, "Optimization of UV curing process", S&T Publishing Inc, 2008, pp. 95-106 (with cover sheet).

* cited by examiner

COMPOUND HAVING POLYCYCLIC AROMATIC SKELETON, AND ENDOPEROXIDE COMPOUND OF SAME

CROSS-REFERENCE TO RELATED APPLICATIONS

The present application is the national stage of international application PCT/JP2019/004912, filed on Feb. 12, 2019.

TECHNICAL FIELD

The present invention relates to a compound having a polycyclic aromatic skeleton and its endoperoxide compound. Particularly, it relates to a compound having a polycyclic aromatic skeleton and its endoperoxide compound and a method for producing it, and a radical polymerizable composition containing a compound having a polycyclic aromatic skeleton and/or its endoperoxide compound.

BACKGROUND ART

In a reaction of forming a polymer compound by polymerization of a radical polymerizable compound, usually, a radical polymerization initiator to initiate the polymerization reaction is used. In a case where light irradiation is employed as a polymerization initiation energy, a photoradical polymerization initiator which absorbs light and decomposes and generates a radical species is used. As the photoradical polymerization initiator, an alkylphenone photoradical polymerization initiator, an acylphosphine oxide photoradical polymerization initiator, an oxime ester photoradical polymerization initiator, etc., have been known. Of such a photoradical polymerization initiator, when absorbs light having a specific wavelength, a bond at a specific portion is cleft, and a radical generates at the cleft portion, which functions as a polymerization initiator to initiate polymerization of a polymerizable compound.

However, it is known that in a radical polymerization reaction using such a radical polymerization initiator, inhibition (oxygen inhibition) by oxygen molecules is problematic. The oxygen inhibition means that a radical species generated from the radical polymerization initiator reacts with for example oxygen atoms dissolved in the radical polymerizable composition and is deactivated, and no radical polymerization rate corresponding to the radical polymerization initiator added can not be obtained and as a result, oxygen molecules act as a radical polymerization inhibitor. Further, in general, such polymerization inhibition by oxygen in known to not only remarkably reduce the radical polymerization rate but also increase the time until initiation of the polymerization that is so-called induction period (IP) (Non-Patent Document 1). Accordingly, in the polymerization reaction of a radical polymerizable compound, polymerization is conduct while oxygen present in the system is removed for example by replacement with nitrogen, or oxygen is shut out by covering the radical polymerizable composition with an oxygen-impermeable film. However, such a method takes time and effort or costs a lot. Accordingly, to reduce the oxygen inhibition, studies have been known such that as the radical polymerizable compound, a compound which is less susceptible to oxygen inhibition is used (e.g. Patent Documents 1 and 2). Further, even when the radical polymerizable composition is covered with an oxygen-impermeable film, oxygen dissolved in the radical polymerizable composition causes polymerization inhibition at the initial stage of the polymerization thereby increases IP. Further, for photo ink jet, photo 3D printers and photo offset printing for which high speed scanning is required, not only a decrease in the polymerization rate but also an increase of IP is a significant problem. Accordingly, a method for further reducing oxygen inhibition, and a radical polymerization initiator and a radical polymerization method which are hardly susceptible to oxygen inhibition, have been desired.

The oxygen molecule which causes the oxygen inhibition in radical polymerization is an oxygen molecule in the ground state, that is triplet oxygen, which has a biradical structure with two unpaired electrons in $\pi y^*$ and $\pi z^*$ orbitals. Thus, triplet oxygen is highly reactive with a radical species and thereby inhibits radical polymerization. On the other hand, an oxygen molecule may also be in a singlet oxygen state which is an excited state, in addition to the triplet oxygen state which is the ground state. Although singlet oxygen is a type of active oxygen, it is known to have no unpaired electron in the orbital and not to have a radical structure, and thereby not to react with a radical species, not to inhibit radical polymerization and not to act as a polymerization inhibitor. Accordingly, oxygen inhibition can be reduced if oxygen in the ground state (triplet oxygen) can be exited to singlet oxygen.

Further, singlet oxygen is known to have electrophilic characteristics and react with olefins, etc. For example, it has been known that an olefin having allylic hydrogen reacts with singlet oxygen to form allyl hydroperoxide, and that singlet oxygen undergoes Diels-Alder addition reaction to a 1,3-conjugated diene to form a 1,4-endoperoxide (Non-Patent Document 2).

Formation of singlet oxygen directly from triplet oxygen in the ground state by excitation corresponds to spin-forbidden transition and does not occur. Accordingly, in general, singlet oxygen is formed by using a dye (photosensitizer) such as rose bengal or methylene blue under irradiation with specific light. That is, it is known that first, the dye as the photosensitizer is excited by light, and the excited species becomes in an excited triplet state by intersystem crossing, triplet-triplet energy transfer from the excited triplet state to triplet oxygen in the ground state of the dye occurs, and simultaneously with return of the dye to the ground state, oxygen is excited to a singlet oxygen molecule (Patent Document 3). On that occasion, the dye acts as a singlet oxygen generator. In this specification, such a compound which excites oxygen in the ground state to convert it to singlet oxygen will be referred to as a singlet oxygen generator.

Further, Patent Document 4 discloses that a photosensitive dye such as a xanthene dye, a thiazine dye or an acridine dye is exposed to light rays having a wavelength of from 300 nm to 1,400 nm to excite oxygen in the ground state to singlet oxygen, which reacts with an olefin and a 1,3-conjugated diene to form a hydroperoxide and a peroxide. The hydroperoxide group functions as a graft moiety to styrene to form a high impact polystyrene having a core-shell structure.

Further, it has been known that the center ring of an anthracene compound behaves as a diene and the anthracene compound reacts with singlet oxygen to form an endoperoxide. For example, it has been known that a 9,10-diphenylanthracene derivative reacts with singlet oxygen to form an endoperoxide (Non-Patent Document 3). In this reaction, the 9,10-diphenylanthracene acts as a singlet oxygen trapper.

In this specification, such a compound which reacts with singlet oxygen to form an endoperoxide will be referred to as a singlet oxygen trapper.

On the other hand, it has been known that an anthracene compound such as a 9,10-dialkoxyanthracene compound or a 9,10-bis(alkoxycarbonyloxy)anthracene compound functions as a photoradical polymerization sensitizer. For example, 9,10-dibutoxyanthracene or 9,10-bisoctanoyloxyanthracene functions as a photopolymerization sensitizer which, in a radical polymerization reaction using a photoradical polymerization initiator, actives the photoradical polymerization initiator so that radical polymerization is possible even with a long wavelength light of 385 nm (Patent Documents 5, 6, 7 and the like).

Further, Patent Document 8 discloses that a 9,10-bis (substituted carbonyloxy)anthracene compound decomposes by itself to generate a radical species and functions as an initiator of radical polymerization.

An example that a 1,4-dialkoxynaphthalene compound is used as a photoradical polymerization sensitizer, and an example that it is used together with a 9,10-dialkoxyanthracene compound as a photoradical polymerization sensitization aid have been known (Patent Documents 9, 10 and 11).

Still further, Patent Document 12 discloses a method for producing an anthracene endoperoxide by reacting a multi-substituted anthracene derivative with oxygen under irradiation with ultraviolet rays.

And, as the heat radical polymerization initiator, in addition to an azo polymerization initiator, a ketone peroxide polymerization initiator, a hydroperoxide polymerization initiator, a dialkyl peroxide polymerization initiator, a peroxyketal polymerization initiator, a peroxy ester polymerization initiator, a peroxy dicarbonate polymerization initiator, a diacyl peroxide polymerization initiator, etc. have been known (Patent Document 13).

PRIOR ART DOCUMENTS

Patent Documents

Patent Document 1: JP-A-2003-206319
Patent Document 2: JP-A-2004-277660
Patent Document 3: JP-A-2008-221159
Patent Document 4: JP-A-2012-514079
Patent Document 5: JP-A-2015-183139
Patent Document 6: JP-A-2017-57249
Patent Document 7: JP-A-2016-84447
Patent Document 8: JP-A-2011-42743
Patent Document 9: JP-A-2015-105292
Patent Document 10: JP-A-2011-246606
Patent Document 11: JP-A-2007-118396
Patent Document 12: JP-A-2003-261572
Patent Document 13: JP-A-2011-236297

Non-Patent Documents

Non-Patent Document 1: GEORGE ODIAN, PRINCIPLES OF POLYMERIZATION Fourth Edition (2004), p. 255-256
Non-Patent Document 2: Masakatsu Matsumoto and Kiyoshi Kondo, Journal of Synthetic Organic Chemistry, Japan, vol. 35, No. 3 (1977), p. 188-200
Non-Patent Document 3: Demet Karaca Balta et al, Macromolecules 2012, 45, p. 119-125
Non-Patent Document 4: Yoshiyuki Kiriyama, "Optimization of UV curing process" p. 95 to 106 (S&T Publishing Inc, 2008)

DISCLOSURE OF INVENTION

Technical Problem

The object of the present invention is to provide a novel radical polymerization method in which in a polymerization reaction of a radical polymerizable compound, oxygen which causes oxygen inhibition is positively utilized to produce an endoperoxide compound having a polycyclic aromatic skeleton from a compound having a polycyclic aromatic skeleton, and the endoperoxide compound having a polycyclic aromatic skeleton is used as a radical polymerization initiator, and further provides a novel radical polymerizable composition using the compound having a polycyclic aromatic skeleton of the present invention, and its polymerization method.

Solution to Problem

The present inventors have conducted extensive studies on the reactivity of the compound having a polycyclic aromatic skeleton with oxygen and as a result, found that in radical polymerization of a radical polymerizable compound in the presence of oxygen, by a specific compound having a polycyclic aromatic skeleton be present and by irradiating the compound with a specific wavelength light, oxygen in the ground state is excited to be singlet oxygen, which reacts with the compound having a polycyclic aromatic skeleton to form an endoperoxide compound having a polycyclic aromatic skeleton. They have further found that the endoperoxide compound having a polycyclic aromatic skeleton has a capability of initiating radical polymerization of a radical polymerizable compound.

That is, the present invention according to a first embodiment resides in an endoperoxide compound having a polycyclic aromatic skeleton represented by the following formula (1):

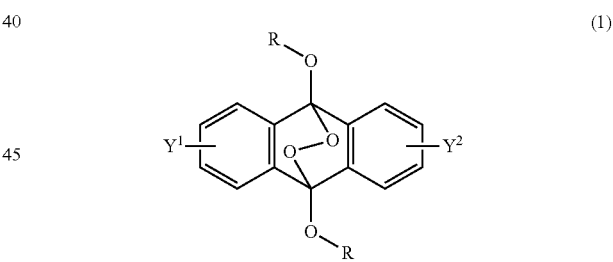

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom.

The present invention according to a second embodiment resides in a method for producing an endoperoxide compound having a polycyclic aromatic skeleton represented by the following formula (1), which comprises reacting a compound having a polycyclic aromatic skeleton represented by the following formula (2) with molecular oxygen under irradiation with light having a peak wavelength within a range of from 300 nm to 410 nm:

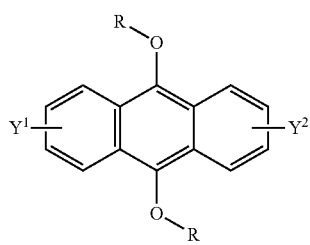

(2)

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom;

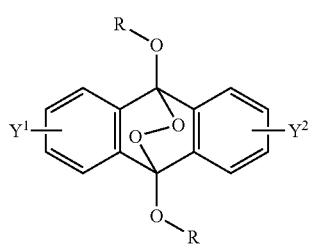

(1)

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom.

The present invention according to a third embodiment resides in a method for producing an endoperoxide compound having a polycyclic aromatic skeleton represented by the following formula (1), which comprises reacting a compound having a polycyclic aromatic skeleton represented by the following formula (2) with singlet oxygen generated by a singlet oxygen generator other than the compound having a polycyclic aromatic skeleton represented by the formula (2) and molecular oxygen in the coexistence of the singlet oxygen generator:

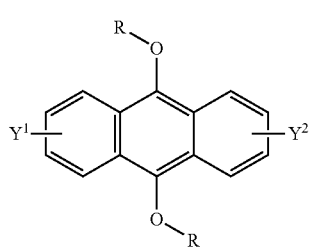

(2)

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom;

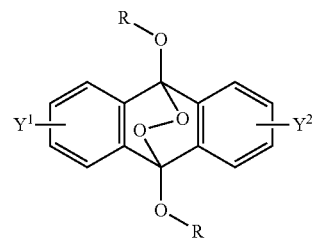

(1)

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom.

The present invention according to a fourth embodiment resides in an endoperoxide compound having a polycyclic aromatic skeleton represented by the following formula (3):

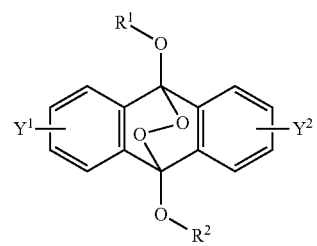

(3)

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

The present invention according to a fifth embodiment resides in a method for producing an endoperoxide compound having a polycyclic aromatic skeleton represented by the following formula (3), which comprises reacting a compound having a polycyclic aromatic skeleton represented by the following formula (4) with molecular oxygen under irradiation with light having a peak wavelength within a range of from 300 nm to 410 nm:

(4)

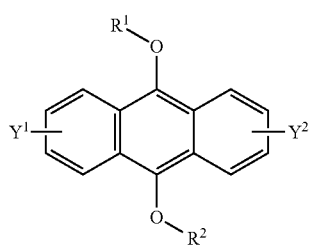

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom;

(3)

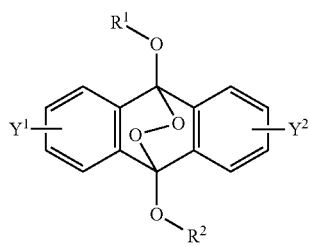

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

The present invention according to a sixth embodiment resides in a method for producing an endoperoxide compound having a polycyclic aromatic skeleton represented by the following formula (3), which comprises reacting a compound having a polycyclic aromatic skeleton represented by the following formula (4) with singlet oxygen generated by a singlet oxygen generator other than the compound having a polycyclic aromatic skeleton represented by the formula (4) and molecular oxygen in the coexistence of the singlet oxygen generator:

(4)

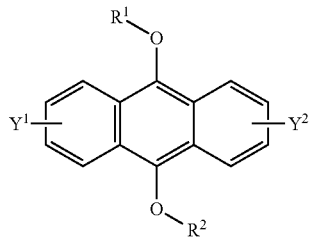

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom;

(3)

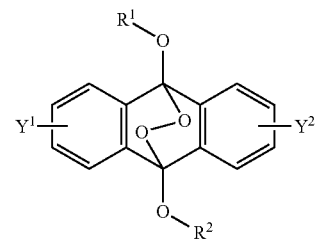

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

The present invention according to a seventh embodiment resides in an endoperoxide compound having a polycyclic aromatic skeleton represented by the following formula (5):

(5)

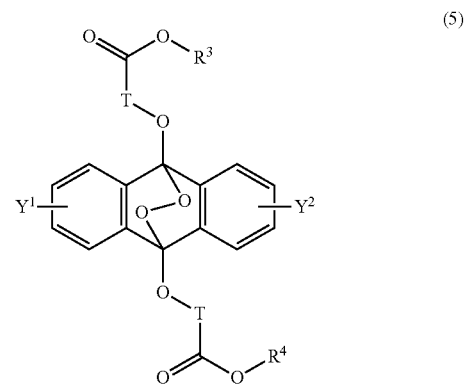

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to an eighth embodiment resides in a method for producing an endoperoxide compound having a polycyclic aromatic skeleton represented by the following formula (5), which comprises reacting a compound having a polycyclic aromatic skeleton represented by the following formula (6) with molecular oxygen under irradiation with light having a peak wavelength within a range of from 300 nm to 410 nm:

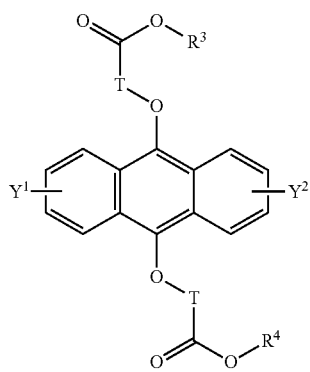

(6)

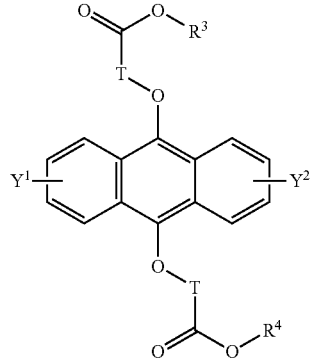

(6)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom;

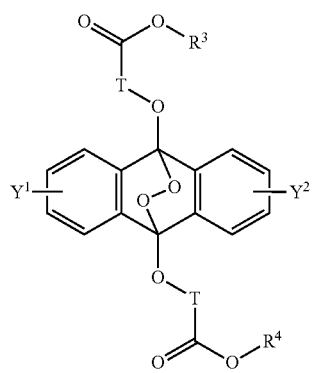

(5)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to a tenth embodiment resides in a compound having a polycyclic aromatic skeleton represented by the following formula (6):

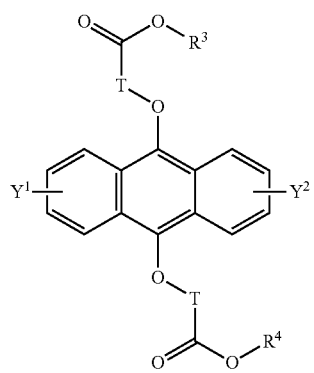

(6)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

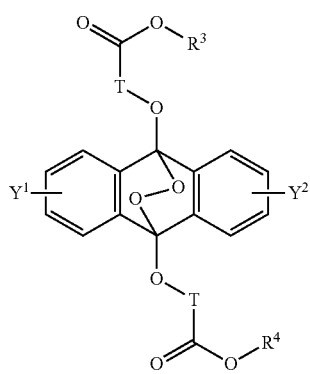

(5)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to a ninth embodiment resides in a method for producing an endoperoxide compound having a polycyclic aromatic skeleton represented by the following formula (5), which comprises reacting a compound having a polycyclic aromatic skeleton represented by the following formula (6) with singlet oxygen generated by a singlet oxygen generator other than the compound having a polycyclic aromatic skeleton represented by the formula (6) and molecular oxygen in the coexistence of the singlet oxygen generator:

The present invention according to an eleventh embodiment resides in the compound having a polycyclic aromatic skeleton represented by the formula (6) according to the tenth embodiment, wherein in the formula (6), T is a methylene group.

The present invention according to a twelfth embodiment resides in a method for producing a compound having a polycyclic aromatic skeleton represented by the following formula (6), which comprises reacting a 9,10-dihydroxyanthracene compound represented by the following formula (7) and a halogenated ester compound:

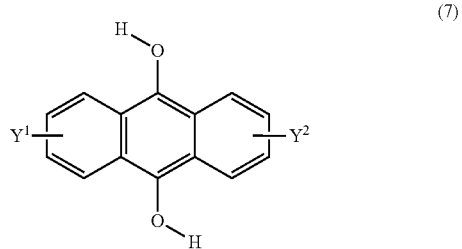

wherein each of $Y^1$ and $Y^2$ is a hydrogen atom, a $C_{1-8}$ alkyl group or a halogen atom;

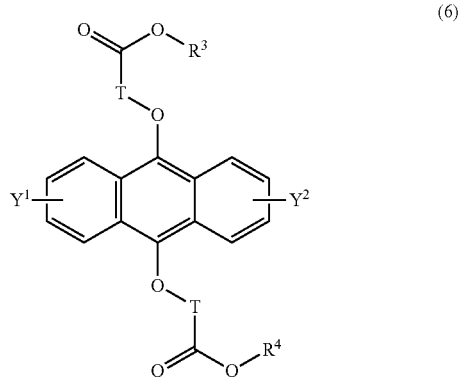

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to a thirteenth embodiment resides in a photoradical polymerization initiator comprising the endoperoxide compound having a polycyclic aromatic skeleton as defined in any one of the first, fourth and seventh embodiments.

The present invention according to a fourteenth embodiment resides in a heat radical polymerization initiator comprising the endoperoxide compound having a polycyclic aromatic skeleton as defined in any one of the first, fourth and seventh embodiments.

The present invention according to a fifteenth embodiment resides in a radical polymerizable composition containing the photoradical polymerization initiator as defined in the thirteenth embodiment and a radical polymerizable compound.

The present invention according to a sixteenth embodiment resides in a radical polymerizable composition containing the heat radical polymerization initiator as defined in the fourteenth embodiment and a radical polymerizable compound.

The present invention according to a seventeenth embodiment resides in the radical polymerizable composition according to the fifteenth embodiment, which further contains a photoradical polymerization sensitizer.

The present invention according to an eighteenth embodiment resides in the radical polymerizable composition according to the sixteenth embodiment, which further contains a decomposition promoter for the heat radical polymerization initiator.

The present invention according to a nineteenth embodiment resides in a method for curing the radical polymerizable composition as defined in the fifteenth or seventeenth embodiment, which comprises irradiating the radical polymerizable composition with energy rays including light having a peak wavelength within a range of from 230 nm to 330 nm to conduct a polymerization reaction.

The present invention according to a twentieth embodiment resides in a method for curing the radical polymerizable composition as defined in the seventeenth embodiment, which comprises irradiating the radical polymerizable composition with energy rays including light having a peak wavelength within a range of from 300 nm to 410 nm to conduct a polymerization reaction.

The present invention according to a twenty-first embodiment resides in a method for curing the radical polymerizable composition as defined in the sixteenth or eighteenth embodiment, which comprises subjecting the radical polymerizable composition to heat treatment to conduct a polymerization reaction.

The present invention according to a twenty-second embodiment resides in a method for curing a radical polymerizable composition, which comprises irradiating a radical polymerizable composition containing a compound having a polycyclic aromatic skeleton represented by the following formula (2) and a radical polymerizable compound, with ultraviolet rays in the presence of oxygen to produce an endoperoxide compound having a polycyclic aromatic skeleton represented by the following formula (1), and conducting a polymerization reaction using the endoperoxide compound having a polycyclic aromatic skeleton as a photoradical polymerization initiator and/or a heat radical polymerization initiator:

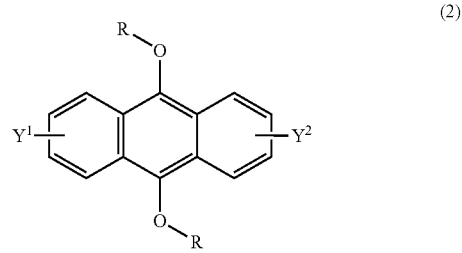

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom;

(1)

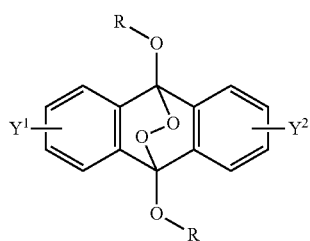

wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group, an aryloxycarbonyl group having a $C_{6-10}$ aryl group, an alkyloxycarbonylmethyl group having a $C_{1-12}$ alkyl group or an aryloxycarbonylmethyl group having a $C_{6-12}$ aryl group, and each of $Y^1$ and $Y^2$ is a hydrogen atom, a $C_{1-8}$ alkyl group or a halogen atom.

The present invention according to a twenty-third embodiment resides in a method for curing a radical polymerizable composition, which comprises irradiating a radical polymerizable composition containing a compound having a polycyclic aromatic skeleton represented by the following formula (4) and a radical polymerizable compound, with ultraviolet rays in the presence of oxygen to produce an endoperoxide compound having a polycyclic aromatic skeleton represented by the following formula (3), and conducting a polymerization reaction using the endoperoxide compound having a polycyclic aromatic skeleton as a photoradical polymerization initiator and/or a heat radical polymerization initiator:

(4)

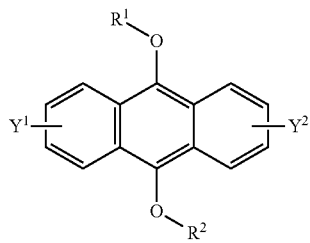

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom;

(3)

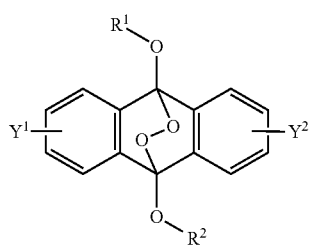

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

The present invention according to a twenty-fourth embodiment resides in a method for curing a radical polymerizable composition, which comprises irradiating a radical polymerizable composition containing a compound having a polycyclic aromatic skeleton represented by the following formula (6) and a radical polymerizable compound, with ultraviolet rays in the presence of oxygen to produce an endoperoxide compound having a polycyclic aromatic skeleton represented by the following formula (5), and conducting a polymerization reaction using the endoperoxide compound having a polycyclic aromatic skeleton as a photoradical polymerization initiator and/or a heat radical polymerization initiator:

(6)

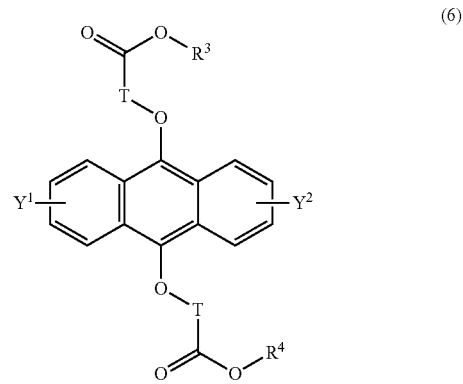

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom;

(5)

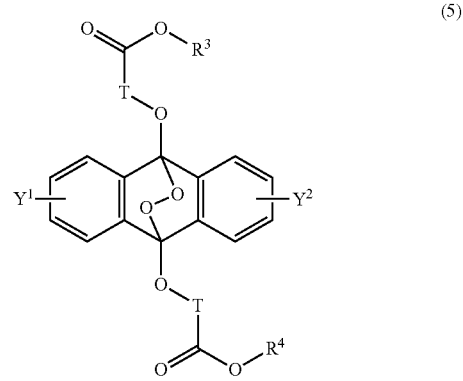

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to a twenty-fifth embodiment resides in the method for curing a radical polymerizable composition according to any one of the twenty-second to twenty-fourth embodiments, wherein the ultraviolet rays applied are light having a peak wavelength within a range of from 300 nm to 410 nm.

The present invention according to a twenty-sixth embodiment resides in a photopolymerization sensitizer containing a compound having a polycyclic aromatic skeleton represented by the following formula (6):

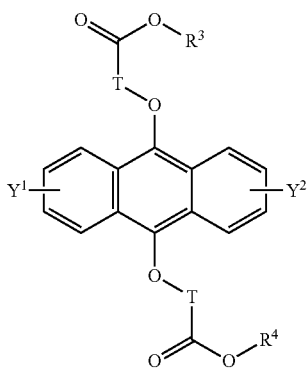

(6)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

The present invention according to a twenty-seventh embodiment resides in the photopolymerization sensitizer according to the twenty-sixth embodiment, wherein in the compound having a polycyclic aromatic skeleton represented by the formula (6), T is a methylene group.

The present invention according to a twenty-eighth embodiment resides in a photopolymerization initiator composition containing the photopolymerization sensitizer as defined in the twenty-sixth or twenty-seventh embodiment and a photopolymerization initiator.

The present invention according to a twenty-ninth embodiment resides in a photopolymerizable composition containing the photopolymerization initiator composition as defined in the twenty-eighth embodiment and a photoradical polymerizable compound.

The present invention according to a thirtieth embodiment resides in a polymerization method of polymerizing the photopolymerizable composition as defined in the twenty-ninth embodiment by irradiating the composition with energy rays including light having a wavelength within a range of from 300 nm to 500 nm.

The present invention according to a thirty-first embodiment resides in the polymerization method according to the thirtieth embodiment, wherein an irradiation source of the energy rays including light having a wavelength within a range of from 300 nm to 500 nm is an ultraviolet LED with a center wavelength of 365 nm, 375 nm, 385 nm, 395 nm or 405 nm, or a 405 nm semiconductor laser.

Advantageous Effects of Invention

The present invention is to provide a new type of radical polymerization initiator that is an endoperoxide compound having a polycyclic aromatic skeleton for radical polymerization of a radical polymerizable compound.

The objects, characteristics and advantages of the present invention will become more apparent by the following detailed description.

Figure 1:
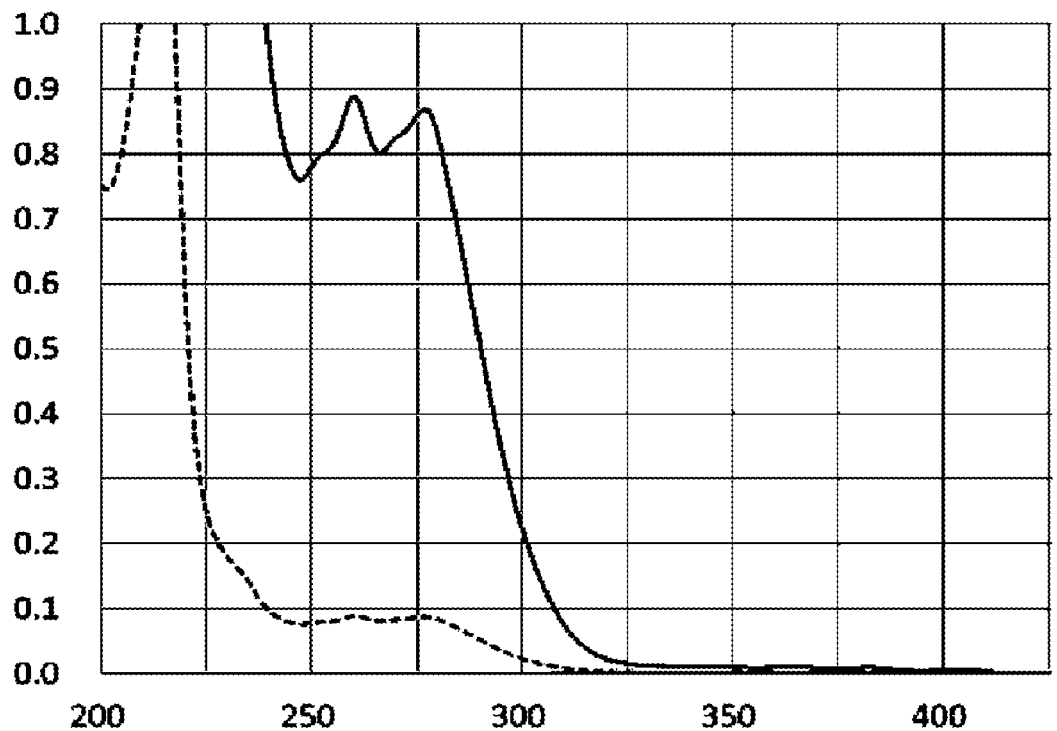
FIG. 1 illustrates light absorption spectra of 9,10-dibutoxyanthracene-9,10-endoperoxide (9,10-dibutoxy-9,10-dihydro-9,10-epidioxyanthracene) (DBAEPO) prepared in Example 1 of the present invention in an ultraviolet region and in a visible region. The vertical axis represents the absorbance, and the horizontal axis represents the wavelength (nm). The solid line in the graph represents the absorbance at DBAEPO 100 ppm at each wavelength, and the broken line represents the absorbance at DBAEPO 10 ppm.
Figure 2:
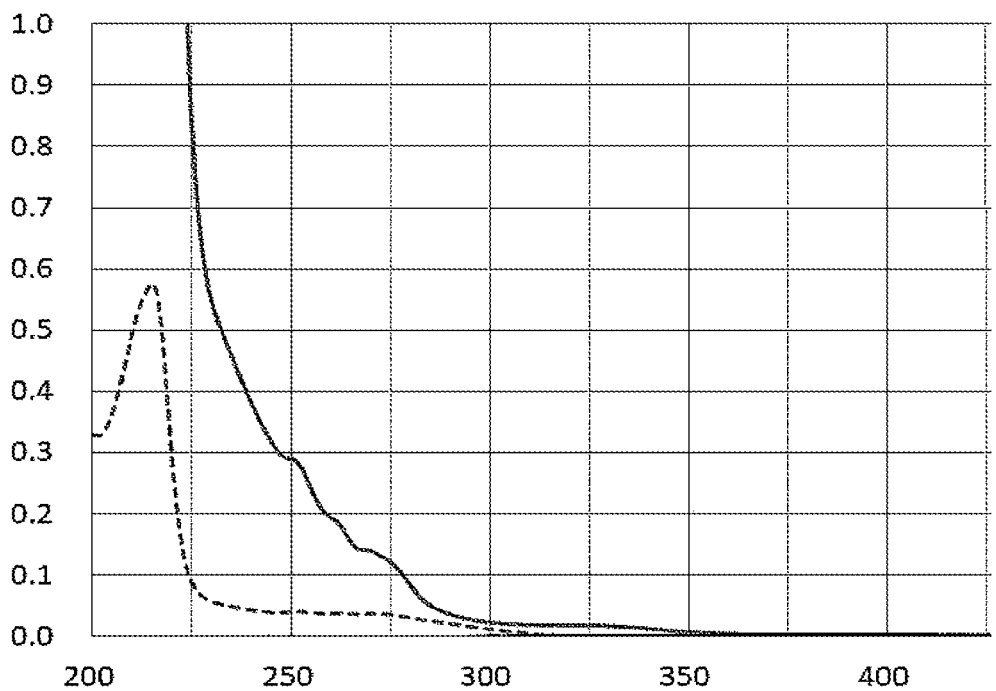
FIG. 2 illustrates light absorption spectra of 9,10-bis(ethoxycarbonylmethyleneoxy)anthracene-9,10-endoperoxide (ECMAEPO) prepared in Example 2 of the present invention in an ultraviolet region and in a visible region. The vertical axis represents the absorbance, and the horizontal axis represents the wavelength (nm). The solid line in the graph represents the absorbance at ECMAEPO 100 ppm at each wavelength, and the broken line represents the absorbance at ECMAEPO 10 ppm.

DESCRIPTION OF EMBODIMENTS (Endoperoxide Compound Having Polycyclic Aromatic Skeleton)

The endoperoxide compound having a polycyclic aromatic skeleton of the present invention has a structure of the above formula (1), (3) or (5):

First, an endoperoxide compound having a polycyclic aromatic skeleton represented by the following formula (3) will be described. The compound of the formula (1) wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, is the endoperoxide compound having a polycyclic aromatic skeleton represented by the formula (3):

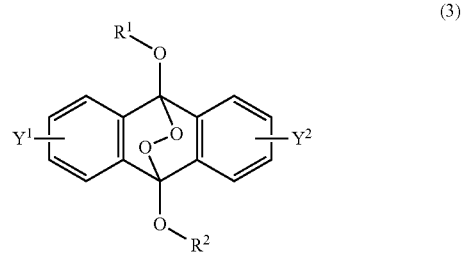

(3)

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

In the formula (3), the $C_{1-20}$ alkyl group as each of $R^1$ and $R^2$ may, for example, be a linear, branched or cyclic alkyl group such as a methyl group, an ethyl group, a n-propyl group, an i-propyl group, a n-butyl group, an i-butyl group, a n-amyl group, an i-amyl group, a n-hexyl group, a n-heptyl group, a n-octyl group, a 2-ethylhexyl group, a n-nonyl group or a n-decyl group. The alkoxymethyl group having a $C_{1-5}$ alkoxy group may, for example, be a methoxymethyl group, an ethoxymethyl group, a n-propoxymethyl group, an i-propoxymethyl group, a n-butoxymethyl group, an i-butoxymethyl group, a n-pentoxymethyl group or an i-pentoxymethyl group. The $C_{6-10}$ aryl group may, for example, be a phenyl group, tolyl group or naphthyl group which may have a substituent. The alkylcarbonyl group having a $C_{1-10}$ alkyl group may, for example, be an acetyl group, a propionyl group, a n-butanoyl group, an iso-butanoyl group, a n-pentanoyl group, a n-hexanoyl group, a n-heptanoyl group, a n-octanoyl group, a 2-ethylhexanoyl group, a n-nonanoyl group or a n-decanoyl group. The arylcarbonyl group having a $C_{6-20}$ aryl group may, for example, be a benzoyl group or a naphthoyl group. The alkyloxycarbonyl group having a $C_{1-10}$ alkyl group may, for example, be a methoxycarbonyl group, an ethoxycarbonyl group, a n-propyloxycarbonyl group, an isopropyloxycarbonyl group, a n-butoxycarbonyl group, an i-butoxycarbonyl group, a sec-butoxycarbonyl group, a tert-butoxycarbonyl group, a n-pentyloxycarbonyl group, a 2,2-dimethylpropyloxycarbonyl group, a cyclopentyloxycarbonyl group, a n-hexyloxycarbonyl group, a cyclohexyloxycarbonyl group, a n-heptyloxycarbonyl group, a 2-methylpentyloxycarbonyl group, a n-octyloxycarbonyl group, a 2-ethylhexyloxycarbonyl group, a n-nonyloxycarbonyl group or a n-decyloxycarbonyl group. The aryloxycarbonyl group having a $C_{6-10}$ aryl group may, for example, be a phenoxycarbonyl group, a 1-naphthyloxycarbonyl group or a 2-naphthyloxycarbonyl group.

In the formula (3), the $C_{1-8}$ alkyl group as each of $Y^1$ and $Y^2$ may, for example, be a methyl group, an ethyl group, a n-propyl group, an i-propyl group, a n-butyl group, an i-butyl group, a n-amyl group, an i-amyl group, a n-hexyl group, a n-heptyl group or a n-octyl group. The halogen atom may be a fluorine atom, a chlorine atom, a bromine atom or an iodine atom.

Now, specific examples of the endoperoxide compound having a polycyclic aromatic skeleton represented by the formula (3) of the present invention will be described. First, examples of the compound of the formula (3) wherein each of $R^1$ and $R^2$ is a $C_{1-10}$ alkyl group or a $C_{6-20}$ aryl group will be described.

For example, 9,10-diethoxyanthracene-9,10-endoperoxide, 9,10-di(n-propoxy)anthracene-9,10-endoperoxide, 9,10-di(i-propoxy)anthracene-9,10-endoperoxide, 9,10-di(n-butoxy)anthracene-9,10-endoperoxide, 9,10-di(i-butoxy)anthracene-9,10-endoperoxide, 9,10-di(n-pentoxy)anthracene-9,10-endoperoxide, 9,10-di(i-pentoxy)anthracene-9,10-endoperoxide, 9,10-di(n-hexyloxy)anthracene-9,10-endoperoxide, 9,10-di(n-heptyloxy)anthracene-9,10-endoperoxide, 9,10-di(n-octyloxy)anthracene-9,10-endoperoxide, 9,10-di(2-ethylhexyloxy)anthracene-9,10-endoperoxide, 9,10-di(n-nonyloxy)anthracene-9,10-endoperoxide, 9,10-dimethoxymethyloxyanthracene-9,10-endoperoxide, 9,10-diethoxymethyloxyanthracene-9,10-endoperoxide, 9,10-dipropoxymethyloxyanthracene-9,10-endoperoxide, 9,10-dibutoxymethyloxyanthracene-9,10-endoperoxide, 9,10-diphenoxyanthracene-9,10-endoperoxide, and 9,10-ditolyloxyanthracene-9,10-endoperoxide may be mentioned.

Further, compounds which are further substituted with an alkyl group, such as 2-methyl-9,10-diethoxyanthracene-9,10-endoperoxide, 2-methyl-9,10-di(n-propoxy)anthracene-9,10-endoperoxide, 2-methyl-9,10-di(i-propoxy)anthracene-9,10-endoperoxide, 2-methyl-9,10-di(n-butoxy)anthracene-9,10-endoperoxide, 2-methyl-9,10-di(i-butoxy)anthracene-9,10-endoperoxide, 2-methyl-9,10-dimethoxymethyloxyanthracene-9,10-endoperoxide, 2-methyl-9,10-diethoxymethyloxyanthracene-9,10-endoperoxide, 2-methyl-9,10-dipropoxymethyloxyanthracene-9,10-endoperoxide, 2-methyl-9,10-dibutoxymethyloxyanthracene-9,10-endoperoxide, 2-methyl-9,10-diphenoxyanthracene-9,10-endoperoxide, 2-methyl-9,10-ditolyloxyanthracene-9,10-endoperoxide, 2-amyl-9,10-dimethoxyanthracene-9,10-endoperoxide, 2-amyl-9,10-diethoxyanthracene-9,10-endoperoxide, 2-amyl-9,10-di(n-propoxy)anthracene-9,10-endoperoxide, 2-amyl-9,10-di(i-propoxy)anthracene-9,10-endoperoxide, 2-amyl-9,10-di(n-butoxy)anthracene-9,10-endoperoxide, and 2-amyl-9,10-di(i-butoxy)anthracene-9,10-endoperoxide may be mentioned.

Further, compounds which are further substituted with a halogen atom, such as 2-chloro-9,10-diethoxyanthracene-9,10-endoperoxide, 2-chloro-9,10-di(n-propoxy)anthracene-9,10-endoperoxide, 2-chloro-9,10-di(i-propoxy)anthracene-9,10-endoperoxide, 2-chloro-9,10-di(n-butoxy)anthracene-9,10-endoperoxide, and 2-chloro-9,10-di(i-butoxy)anthracene-9,10-endoperoxide may be mentioned.

Now, examples of the compound of the formula (3) wherein each of $R^1$ and $R^2$ is an alkylcarbonyl group having a $C_{1-10}$ alkyl group or an arylcarbonyl group having a 6-20 aryl group will be described.

Specific examples include 9,10-diacetyloxyanthracene-9,10-endoperoxide, 9,10-dipropionyloxyanthracene-9,10-endoperoxide, 9,10-bis(n-butanoyloxy)anthracene-9,10-endoperoxide, 9,10-bis(iso-butanoyloxy)anthracene-9,10-endoperoxide, 9,10-bis(n-pentanoyloxy)anthracene-9,10-endoperoxide, 9,10-bis(n-hexanoyloxy)anthracene-9,10-endoperoxide, 9,10-bis(n-heptanoyloxy)anthracene-9,10-endoperoxide, 9,10-bis(n-octanoyloxy)anthracene-9,10-endoperoxide, 9,10-bis(2-ethylhexanoyloxy)anthracene-9,10-endoperoxide, 9,10-bis(n-nonanoyloxy)anthracene-9,10-endoperoxide, 9,10-bis(n-decanoyloxy)anthracene-9,10-endoperoxide, and 9,10-bis(n-dodecanoyloxy)anthracene-9,10-endoperoxide.

Further, compounds which are further substituted with an alkyl group, such as 1-methyl-9,10-diacetyloxyanthracene-9,10-endoperoxide, 1-methyl-9,10-dipropionyloxyanthracene-9,10-endoperoxide, 1-methyl-9,10-bis(n-butanoyloxy)anthracene-9,10-endoperoxide, 1-methyl-9,10-bis(iso-butanoyloxy)anthracene-9,10-endoperoxide, 1-methyl-9,10-bis(n-hexanoyloxy)anthracene-9,10-endoperoxide, 1-methyl-9,10-bis(n-heptanoyloxy)anthracene-9,10-endoperoxide, 1-methyl-9,10-bis(n-octanoyloxy)anthracene-9,10-endoperoxide, 2-methyl-9,10-diacetyloxyanthracene-9,10-endoperoxide, 2-methyl-9,10-dipropionyloxyanthracene-9,10-endoperoxide, 2-methyl-9,10-bis(n-butanoyloxy)anthracene-9,10-endoperoxide, 2-methyl-9,10-bis(iso-butanoyloxy)anthracene-9,10-endoperoxide, 2-methyl-9,10-bis(n-hexanoyloxy)anthracene-9,10-endoperoxide, 2-methyl-9,10-bis(n-heptanoyloxy)anthracene-9,10-endoperoxide, 2-methyl-9,10-bis(n-octanoyloxy)anthracene-9,10-endoperoxide, 1-ethyl-9,10-diacetyloxyanthracene-9,10-endoperoxide, 1-ethyl-9,10-dipropionyloxyanthracene-9,10-endoperoxide, 1-ethyl-9,10-bis(n-butanoyloxy)anthracene-9,10-endoperoxide, 1-ethyl-9,10-bis(iso-butanoyloxy)anthracene-9,10-endoperoxide, 1-ethyl-9,10-bis(n-hexanoyloxy)anthracene-9,10-endoperoxide, 1-ethyl-9,10-bis(n-heptanoyloxy)anthracene-9,10-endoperoxide, 1-ethyl-9,10-bis(n-octanoyloxy)anthracene-9,10-endoperoxide, 2-ethyl-9,10-diacetyloxyanthracene-9,10-endoperoxide, 2-ethyl-9,10-dipropionyloxyanthracene-9,10-endoperoxide, 2-ethyl-9,10-bis(n-butanoyloxy)anthracene-9,10-endoperoxide, 2-ethyl-9,10-bis(iso-butanoyloxy)anthracene-9,10-endoperoxide, 2-ethyl-9,10-bis(n-hexanoyloxy)anthracene-9,10-endoperoxide, 2-ethyl-9,10-bis(n-heptanoyloxy)

anthracene-9,10-endoperoxide, and 2-ethyl-9,10-bis(n-octanoyloxy)anthracene-9,10-endoperoxide may be mentioned.

Further, 2,3-dimethyl-9,10-diacetyloxyanthracene-9,10-endoperoxide, 2,3-dimethyl-9,10-dipropionyloxyanthracene-9,10-endoperoxide, 2,3-dimethyl-9,10-bis(n-butanoyloxy)anthracene-9,10-endoperoxide, 2,3-dimethyl-9,10-bis(iso-butanoyloxy)anthracene-9,10-endoperoxide, 2,3-dimethyl-9,10-bis(n-hexanoyloxy)anthracene-9,10-endoperoxide, 2,3-dimethyl-9,10-bis(n-heptanoyloxy)anthracene-9,10-endoperoxide, 2,3-dimethyl-9,10-bis(n-octanoyloxy)anthracene-9,10-endoperoxide, 2,6-dimethyl-9,10-diacetyloxyanthracene-9,10-endoperoxide, 2,6-dimethyl-9,10-dipropionyloxyanthracene-9,10-endoperoxide, 2,6-dimethyl-9,10-bis(n-butanoyloxy)anthracene-9,10-endoperoxide, 2,6-dimethyl-9,10-bis(iso-butanoyloxy)anthracene-9,10-endoperoxide, 2,6-dimethyl-9,10-bis(n-hexanoyloxy)anthracene-9,10-endoperoxide, 2,6-dimethyl-9,10-bis(n-heptanoyloxy)anthracene-9,10-endoperoxide, and 2,6-dimethyl-9,10-bis(n-octanoyloxy)anthracene-9,10-endoperoxide may, for example, be mentioned.

Now, examples of the compound of the formula (3) wherein each of $R^1$ and $R^2$ is an alkyloxycarbonyl group having a $C_{1-10}$ alkyl group or an aryloxycarbonyl group having a $C_{6-20}$ aryl group may be mentioned.

Specific examples include 9,10-bis(methoxycarbonyloxy)anthracene-9,10-endoperoxide, 9,10-bis(ethoxycarbonyloxy)anthracene-9,10-endoperoxide, 9,10-bis(n-propoxycarbonyloxy)anthracene-9,10-endoperoxide, 9,10-bis(i-propoxycarbonyloxy)anthracene-9,10-endoperoxide, 9,10-bis(n-butoxycarbonyloxy)anthracene-9,10-endoperoxide, and 9,10-bis(i-butoxycarbonyloxy)anthracene-9,10-endoperoxide.

Further, compounds which are further substituted with an alkyl group, such as 1-methyl-9,10-bis(methoxycarbonyloxy)anthracene-9,10-endoperoxide, 1-methyl-9,10-bis(ethoxycarbonyloxy)anthracene-9,10-endoperoxide, 1-methyl-9,10-bis(n-propoxycarbonyloxy)anthracene-9,10-endoperoxide, 1-methyl-9,10-bis(i-propoxycarbonyloxy)anthracene-9,10-endoperoxide, 1-methyl-9,10-bis(n-butoxycarbonyloxy)anthracene-9,10-endoperoxide, 1-methyl-9,10-bis(i-butoxycarbonyloxy)anthracene-9,10-endoperoxide, 2-methyl-9,10-bis(m ethoxycarbonyloxy)anthracene-9,10-endoperoxide, 2-methyl-9,10-bis(ethoxycarbonyloxy)anthracene-9,10-endoperoxide, 2-methyl-9,10-bis(n-propoxycarbonyloxy)anthracene-9,10-endoperoxide, 2-methyl-9,10-bis(i-propoxycarbonyloxy)anthracene-9,10-endoperoxide, 2-methyl-9,10-bis(n-butoxycarbonyloxy)anthracene-9,10-endoperoxide, 2-methyl-9,10-bis(i-butoxycarbonyloxy)anthracene-9,10-endoperoxide, 1-ethyl-9,10-bis(methoxycarbonyloxy)anthracene-9,10-endoperoxide, 1-ethyl-9,10-bis(ethoxycarbonyloxy)anthracene-9,10-endoperoxide, 1-ethyl-9,10-bis(n-propoxycarbonyloxy)anthracene-9,10-endoperoxide, 1-ethyl-9,10-bis(i-propoxycarbonyloxy)anthracene-9,10-endoperoxide, 1-ethyl-9,10-bis(n-butoxycarbonyloxy)anthracene-9,10-endoperoxide, 1-ethyl-9,10-bis(i-butoxycarbonyloxy)anthracene-9,10-endoperoxide, 2-ethyl-9,10-bis(methoxycarbonyloxy)anthracene-9,10-endoperoxide, 2-ethyl-9,10-bis(ethoxycarbonyloxy)anthracene-9,10-endoperoxide, 2-ethyl-9,10-bis(n-propoxycarbonyloxy)anthracene-9,10-endoperoxide, 2-ethyl-9,10-bis(i-propoxycarbonyloxy)anthracene-9,10-endoperoxide, 2-ethyl-9,10-bis(n-butoxycarbonyloxy)anthracene-9,10-endoperoxide, and 2-ethyl-9,10-bis(i-butoxycarbonyloxy)anthracene-9,10-endoperoxide may be mentioned.

Further, 2,3-dimethyl-9,10-bis(methoxycarbonyloxy)anthracene-9,10-endoperoxide, 2,3-dimethyl-9,10-bis(ethoxycarbonyloxy)anthracene-9,10-endoperoxide, 2,3-dimethyl-9,10-bis(n-propoxycarbonyloxy)anthracene-9,10-endoperoxide, 2,3-dimethyl-9,10-bis(i-propoxycarbonyloxy)anthracene-9,10-endoperoxide, 2,3-dimethyl-9,10-bis(n-butoxycarbonyloxy)anthracene-9,10-endoperoxide, 2,3-dimethyl-9,10-bis(i-butoxycarbonyloxy)anthracene-9,10-endoperoxide, 2,6-dimethyl-9,10-bis(methoxycarbonyloxy)anthracene-9,10-endoperoxide, 2,6-dimethyl-9,10-bis(ethoxycarbonyloxy)anthracene-9,10-endoperoxide, 2,6-dimethyl-9,10-bis(n-propoxycarbonyloxy)anthracene-9,10-endoperoxide, 2,6-dimethyl-9,10-bis(i-propoxycarbonyloxy)anthracene-9,10-endoperoxide, 2,6-dimethyl-9,10-bis(n-butoxycarbonyloxy)anthracene-9,10-endoperoxide, 2,6-dimethyl-9,10-bis(i-butoxycarbonyloxy)anthracene-9,10-endoperoxide, 2,7-dimethyl-9,10-bis(methoxycarbonyloxy)anthracene-9,10-endoperoxide, 2,7-dimethyl-9,10-bis(ethoxycarbonyloxy)anthracene-9,10-endoperoxide, 2,7-dimethyl-9,10-bis(n-propoxycarbonyloxy)anthracene-9,10-endoperoxide, 2,7-dimethyl-9,10-bis(i-propoxycarbonyloxy)anthracene-9,10-endoperoxide, 2,7-dimethyl-9,10-bis(n-butoxycarbonyloxy)anthracene-9,10-endoperoxide, 2,7-dimethyl-9,10-bis(i-butoxycarbonyloxy)anthracene-9,10-endoperoxide, 1,5-dimethyl-9,10-bis(methoxycarbonyloxy)anthracene-9,10-endoperoxide, 1,5-dimethyl-9,10-bis(ethoxycarbonyloxy)anthracene-9,10-endoperoxide, 1,5-dimethyl-9,10-bis(n-propoxycarbonyloxy)anthracene-9,10-endoperoxide, 1,5-dimethyl-9,10-bis(i-propoxycarbonyloxy)anthracene-9,10-endoperoxide, 1,5-dimethyl-9,10-bis(n-butoxycarbonyloxy)anthracene-9,10-endoperoxide, and 1,5-dimethyl-9,10-bis(i-butoxycarbonyloxy)anthracene-9,10-endoperoxide may, for example, be mentioned.

Still further, 2,3-diethyl-9,10-bis(methoxycarbonyloxy)anthracene-9,10-endoperoxide, 2,3-diethyl-9,10-bis(ethoxycarbonyloxy)anthracene-9,10-endoperoxide, 2,3-diethyl-9,10-bis(n-propoxycarbonyloxy)anthracene-9,10-endoperoxide, 2,3-diethyl-9,10-bis(i-propoxycarbonyloxy)anthracene-9,10-endoperoxide, 2,3-diethyl-9,10-bis(n-butoxycarbonyloxy)anthracene-9,10-endoperoxide, 2,3-diethyl-9,10-bis(i-butoxycarbonyloxy)anthracene-9,10-endoperoxide, 2,6-diethyl-9,10-bis(methoxycarbonyloxy)anthracene-9,10-endoperoxide, 2,6-diethyl-9,10-bis(ethoxycarbonyloxy)anthracene-9,10-endoperoxide, 2,6-diethyl-9,10-bis(n-propoxycarbonyloxy)anthracene-9,10-endoperoxide, 2,6-diethyl-9,10-bis(i-propoxycarbonyloxy)anthracene-9,10-endoperoxide, 2,6-diethyl-9,10-bis(n-butoxycarbonyloxy)anthracene-9,10-endoperoxide, 2,6-diethyl-9,10-bis(i-butoxycarbonyloxy)anthracene-9,10-endoperoxide, 2,7-diethyl-9,10-bis(methoxycarbonyloxy)anthracene-9,10-endoperoxide, 2,7-diethyl-9,10-bis(ethoxycarbonyloxy)anthracene-9,10-endoperoxide, 2,7-diethyl-9,10-bis(n-propoxycarbonyloxy)anthracene-9,10-endoperoxide, 2,7-diethyl-9,10-bis(i-propoxycarbonyloxy)anthracene-9,10-endoperoxide, 2,7-diethyl-9,10-bis(n-butoxycarbonyloxy)anthracene-9,10-endoperoxide, 2,7-diethyl-9,10-bis(i-butoxycarbonyloxy)anthracene-9,10-endoperoxide, 1,5-diethyl-9,10-bis(methoxycarbonyloxy)anthracene-9,10-endoperoxide, 1,5-diethyl-9,10-bis(ethoxycarbonyloxy)anthracene-9,10-endoperoxide, 1,5-diethyl-9,10-bis(n-propoxycarbonyloxy)anthracene-9,10-endoperoxide, 1,5-diethyl-9,10-bis(i-propoxycarbonyloxy)anthracene-9,10-endoperoxide, 1,5-diethyl-9,10-bis(n-butoxycarbonyloxy)anthracene-9,10-endoperoxide, and 1,5-diethyl-9,10-bis(i-butoxycarbonyloxy)anthracene-9,10-endoperoxide may, for example, be mentioned.

Now, the endoperoxide compound having a polycyclic aromatic skeleton represented by the following formula (5) will be described. The compound of the formula (1) wherein R is an alkyloxycarbonylmethyl group having a $C_{1-12}$ alkyl group or an aryloxycarbonylmethyl group having a $C_{6-12}$ aryl group is the compound of the formula (5):

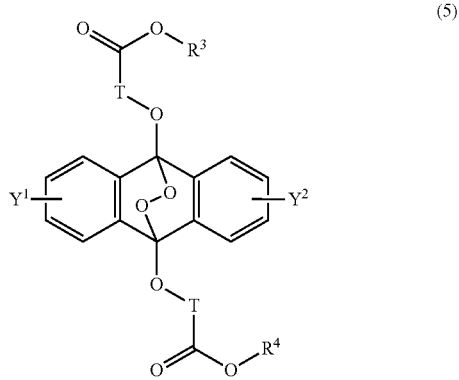

(5)

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

In the formula (5), the $C_{1-20}$ alkylene group as T may, for example, be a methylene group, an ethylene group, a propylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group or an eicosylene group, and the alkylene group may be branched by an alkyl group.

In the formula (5), the $C_{1-20}$ alkyl group as each of $R^3$ and $R^4$ may, for example, be a methyl group, an ethyl group, a n-propyl group, an i-propyl group, a n-butyl group, an i-butyl group, a t-butyl group, a n-pentyl group, an i-pentyl group, a n-hexyl group, a n-heptyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group or a n-eicosyl group.

In the formula (5), the $C_{1-8}$ alkyl group as each of $Y^1$ and $Y^2$ may, for example, be a methyl group, an ethyl group, a n-propyl group, an i-propyl group, a n-butyl group, an i-butyl group, a n-amyl group, an i-amyl group, a n-hexyl group, a n-heptyl group or a n-octyl group. Further, the halogen atom may be a fluorine atom, a chlorine atom, a bromine atom or an iodine atom.

Now, specific examples of the endoperoxide compound having a polycyclic aromatic skeleton represented by the formula (5) of the present invention will be described. The specific examples include 9,10-bis(methoxycarbonylmethyleneoxy)anthracene-9,10-endoperoxide, 9,10-bis(ethoxycarbonylmethyleneoxy)anthracene-9,10-endoperoxide, 9,10-bis(isopropoxycarbonylmethyleneoxy)anthracene-9,10-endoperoxide, 9,10-bis(tert-butoxycarbonylmethyleneoxy)anthracene-9,10-endoperoxide, 9,10-bis(n-butoxycarbonylmethyleneoxy)anthracene-9,10-endoperoxide, 9,10-bis(methoxycarbonylpropyleneoxy)anthracene-9,10-endoperoxide, 9,10-bis(ethoxycarbonylpropyleneoxy)anthracene-9,10-endoperoxide, 9,10-bis(isopropoxycarbonylpropyleneoxy)anthracene-9,10-endoperoxide, 9,10-bis(tert-butoxycarbonylpropyleneoxy)anthracene-9,10-endoperoxide, and 9,10-bis(n-butoxycarbonylpropyleneoxy)anthracene-9,10-endoperoxide.

Specific examples of the compound wherein $Y^1$ or $Y^2$ is an alkyl group include 2-ethyl-9,10-bis(methoxycarbonylmethyleneoxy)anthracene-9,10-endoperoxide, 2-ethyl-9,10-bis(ethoxycarbonylmethyleneoxy)anthracene-9,10-endoperoxide, 2-ethyl-9,10-bis(isopropoxycarbonylmethyleneoxy)anthracene-9,10-endoperoxide, 2-ethyl-9,10-bis(tert-butoxycarbonylmethyleneoxy)anthracene-9,10-endoperoxide, 2-ethyl-9,10-bis(n-butoxycarbonylmethyleneoxy)anthracene-9,10-endoperoxide, 2-ethyl-9,10-bis(methoxycarbonylpropyleneoxy)anthracene-9,10-endoperoxide, 2-ethyl-9,10-bis(ethoxycarbonylpropyleneoxy)anthracene-9,10-endoperoxide, 2-ethyl-9,10-bis(isopropoxycarbonylpropyleneoxy)anthracene-9,10-endoperoxide, 2-ethyl-9,10-bis(tert-butoxycarbonylpropyleneoxy)anthracene-9,10-endoperoxide, and 2-ethyl-9,10-bis(n-butoxycarbonylpropyleneoxy)anthracene-9,10-endoperoxide.

Specific examples of the compound wherein $Y^1$ or $Y^2$ is a halogen atom include 2-chloro-9,10-bis(methoxycarbonylmethyleneoxy)anthracene-9,10-endoperoxide, 2-chloro-9,10-bis(ethoxycarbonylmethyleneoxy)anthracene-9,10-endoperoxide, 2-chloro-9,10-bis(isopropoxycarbonylmethyleneoxy)anthracene-9,10-endoperoxide, 2-chloro-9,10-bis(tert-butoxycarbonylmethyleneoxy)anthracene-9,10-endoperoxide, 2-chloro-9,10-bis(n-butoxycarbonylmethyleneoxy)anthracene-9,10-endoperoxide, 2-chloro-9,10-bis(methoxycarbonylpropyleneoxy)anthracene-9,10-endoperoxide, 2-chloro-9,10-bis(ethoxycarbonylpropyleneoxy)anthracene-9,10-endoperoxide, 2-chloro-9,10-bis(isopropoxycarbonylpropyleneoxy)anthracene-9,10-endoperoxide, 2-chloro-9,10-bis(tert-butoxycarbonylpropyleneoxy)anthracene-9,10-endoperoxide, and 2-chloro-9,10-bis(n-butoxycarbonylpropyleneoxy)anthracene-9,10-endoperoxide.

(Method for Producing Endoperoxide Compound Having Polycyclic Aromatic Skeleton)

Now, the method for producing the endoperoxide compound having a polycyclic aromatic skeleton of the present invention will be described. The endoperoxide compound having a polycyclic aromatic skeleton of the present invention is produced by a reaction of the corresponding compound having a polycyclic aromatic skeleton and singlet oxygen.

(Compound Having Polycyclic Aromatic Skeleton)

The compound having a polycyclic aromatic skeleton used as the raw material in the present invention is a compound having a structure of the formula (2), (4) or (6). The compound of the formula (2) wherein R is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C^{6-10}$ aryl group, is the compound having a polycyclic aromatic skeleton represented by the formula (4). First, the compound having a polycyclic aromatic skeleton represented by the following formula (4) will be described.

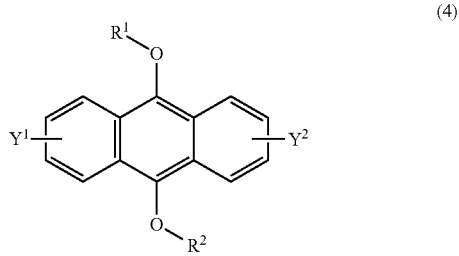

(4)

wherein each of $R^1$ and $R^2$ is a $C_{1-10}$ alkyl group, an alkoxymethyl group having a $C_{1-5}$ alkoxy group, a $C_{6-10}$ aryl group, an alkylcarbonyl group having a $C_{1-10}$ alkyl group, an arylcarbonyl group having a $C_{6-20}$ aryl group, an alkyloxycarbonyl group having a $C_{1-10}$ alkyl group or an aryloxycarbonyl group having a $C_{6-10}$ aryl group, and each of $Y^1$ and $Y^2$ is a hydrogen atom, a $C_{1-8}$ alkyl group or a halogen atom.

Specific examples of $R^1$, $R^2$, $Y^1$ and $Y^2$ in the formula (4) are the same as the specific examples of $R^1$, $R^2$, $Y^1$ and $Y^2$ described for the formula (3).

Specific examples of the formula (4) include 9,10-diethoxyanthracene, 9,10-di(n-propoxy)anthracene, 9,10-di(i-propoxy)anthracene, 9,10-di(n-butoxy)anthracene, 9,10-di(i-butoxy)anthracene, 9,10-di(n-pentoxy)anthracene, 9,10-di(i-pentoxy)anthracene, 9,10-di(n-hexyloxy)anthracene, 9,10-di(n-heptyloxy)anthracene, 9,10-di(n-octyloxy)anthracene, 9,10-di(2-ethylhexyloxy)anthracene, 9,10-di(n-nonyloxy)anthracene, 9,10-dimethoxymethyloxyanthracene, 9,10-diethoxymethyloxyanthracene, 9,10-dipropoxymethyloxyanthracene, 9,10-dibutoxymethyloxyanthracene, 9,10-diphenoxyanthracene, and 9,10-ditolyloxyanthracene.

Further, compounds which are further substituted with an alkyl group, such as 2-methyl-9,10-diethoxyanthracene, 2-methyl-9,10-di(n-propoxy)anthracene, 2-methyl-9,10-di(i-propoxy)anthracene, 2-methyl-9,10-di(n-butoxy)anthracene, 2-methyl-9,10-di(i-butoxy)anthracene, 2-methyl-9,10-dimethoxymethyloxyanthracene, 2-methyl-9,10-diethoxymethyloxyanthracene, 2-methyl-9,10-dipropoxymethyloxyanthracene, 2-methyl-9,10-dibutoxymethyloxyanthracene, 2-methyl-9,10-diphenoxyanthracene, 2-methyl-9,10-ditolyloxyanthracene, 2-amyl-9,10-dimethoxyanthracene, 2-amyl-9,10-diethoxyanthracene, 2-amyl-9,10-di(n-propoxy)anthracene, 2-amyl-9,10-di(i-propoxy)anthracene, 2-amyl-9,10-di(n-butoxy)anthracene, 2-amyl-9,10-di(i-butoxy)anthracene, 2-amyl-9,10-dimethoxymethyloxyanthracene, 2-amyl-9,10-diethoxymethyloxyanthracene, 2-amyl-9,10-dipropoxymethyloxyanthracene, 2-amyl-9,10-dibutoxymethyloxyanthracene, 2-amyl-9,10-diphenoxyanthracene, and 2-amyl-9,10-ditolyloxyanthracene may be mentioned.

Further, compounds which are further substituted with a halogen atom such as 2-chloro-9,10-dimethoxyanthracene, 2-chloro-9,10-diethoxyanthracene, 2-chloro-9,10-di(n-propoxy)anthracene, 2-chloro-9,10-di(i-propoxy)anthracene, 2-chloro-9,10-di(n-butoxy)anthracene, 2-chloro-9,10-di(i-butoxy)anthracene, 2-chloro-9,10-dimethoxymethyloxyanthracene, 2-chloro-9,10-diethoxymethyloxyanthracene, 2-chloro-9,10-dipropoxymethyloxyanthracene, 2-chloro-9,10-dibutoxymethyloxyanthracene, 2-chloro-9,10-diphenoxyanthracene, and 2-chloro-9,10-ditolyloxyanthracene may be mentioned.

Now, examples of the compound of the formula (4) wherein each of $R^1$ and $R^2$ is an alkylcarbonyl group having a $C_{1-10}$ alkyl group or an arylcarbonyl group having a $C_{6-20}$ aryl group may be mentioned.

Specific examples include 9,10-diacetyloxyanthracene, 9,10-dipropionyloxyanthracene, 9,10-bis(n-butanoyloxy) anthracene, 9,10-bis(iso-butanoyloxy)anthracene, 9,10-bis (n-pentanoyloxy)anthracene, 9,10-bis(n-hexanoyloxy)anthracene, 9,10-bis(n-heptanoyloxy)anthracene, 9,10-bis(n-octanoyloxy)anthracene, 9,10-bis(2-ethylhexanoyloxy) anthracene, 9,10-bis(n-nonanoyloxy)anthracene, 9,10-bis(n-decanoyloxy)anthracene, and 9,10-bis(n-dodecanoyloxy) anthracene.

Further, compounds which are further substituted with an alkyl group such as 1-methyl-9,10-diacetyloxyanthracene, 1-methyl-9,10-dipropionyloxyanthracene, 1-methyl-9,10-bis(n-butanoyloxy)anthracene, 1-methyl-9,10-bis(iso-butanoyloxy)anthracene, 1-methyl-9,10-bis(n-hexanoyloxy) anthracene, 1-methyl-9,10-bis(n-heptanoyloxy)anthracene, 1-methyl-9,10-bis(n-octanoyloxy)anthracene, 2-methyl-9, 10-diacetyloxyanthracene, 2-methyl-9,10-dipropionyloxyanthracene, 2-methyl-9,10-bis(n-butanoyloxy)anthracene, 2-methyl-9,10-bis(iso-butanoyloxy)anthracene, 2-methyl-9, 10-bis(n-hexanoyloxy)anthracene, 2-methyl-9,10-bis(n-heptanoyloxy)anthracene, 2-methyl-9,10-bis(n-octanoyloxy)anthracene, 1-ethyl-9,10-diacetyloxyanthracene, 1-ethyl-9,10-dipropionyloxyanthracene, 1-ethyl-9,10-bis(n-butanoyloxy)anthracene, 1-ethyl-9,10-bis(iso-butanoyloxy) anthracene, 1-ethyl-9,10-bis(n-hexanoyloxy)anthracene, 1-ethyl-9,10-bis(n-heptanoyloxy)anthracene, 1-ethyl-9,10-bis(n-octanoyloxy)anthracene, 2-ethyl-9,10-diacetyloxyanthracene, 2-ethyl-9,10-dipropionyloxyanthracene, 2-ethyl-9, 10-bis(n-butanoyloxy)anthracene, 2-ethyl-9,10-bis(iso-butanoyloxy)anthracene, 2-ethyl-9,10-bis(n-hexanoyloxy) anthracene, 2-ethyl-9,10-bis(n-heptanoyloxy)anthracene, and 2-ethyl-9,10-bis(n-octanoyloxy)anthracene may be mentioned.

Still further, 2,3-dimethyl-9,10-diacetyloxyanthracene, 2,3-dimethyl-9,10-dipropionyloxyanthracene, 2,3-dimethyl-9,10-bis(n-butanoyloxy)anthracene, 2,3-dimethyl-9,10-bis (iso-butanoyloxy)anthracene, 2,3-dimethyl-9,10-bis(n-hexanoyloxy)anthracene, 2,3-dimethyl-9,10-bis(n-heptanoyloxy)anthracene, 2,3-dimethyl-9,10-bis(n-octanoyloxy)anthracene, 2,6-dimethyl-9,10-diacetyloxyanthracene, 2,6-dimethyl-9,10-dipropionyloxyanthracene, 2,6-dimethyl-9,10-bis(n-butanoyloxy)anthracene, 2,6-dimethyl-9,10-bis(iso-butanoyloxy)anthracene, 2,6-dimethyl-9,10-bis(n-hexanoyloxy)anthracene, 2,6-dimethyl-9,10-bis(n-heptanoyloxy)anthracene, 2,6-dimethyl-9,10-bis(n-octanoyloxy)anthracene, 2,7-dimethyl-9,10-diacetyloxyanthracene, 2,7-dimethyl-9,10-dipropionyloxyanthracene, 2,7-dimethyl-9,10-bis(n-butanoyloxy)anthracene, 2,7-dimethyl-9,10-bis(iso-butanoyloxy)anthracene, 2,7-dimethyl-9,10-bis(n-hexanoyloxy)anthracene, 2,7-dimethyl-9,10-bis(n-heptanoyloxy)anthracene, and 2,7-dimethyl-9,10-bis(n-octanoyloxy)anthracene may, for example be mentioned.

Now, examples of the compound of the formula (4) wherein each of $R^1$ and $R^2$ is an alkyloxycarbonyl group having a $C_{1-10}$ alkyl group or an aryloxycarbonyl group having a $C_{6-20}$ aryl group may be mentioned.

Specific examples include 9,10-bis(methoxycarbonyloxy) anthracene, 9,10-bis(ethoxycarbonyloxy)anthracene, 9,10- bis(n-propoxycarbonyloxy)anthracene, 9,10-bis(i-propoxycarbonyloxy)anthracene, 9,10-bis(n-butoxycarbonyloxy)anthracene, 9,10-bis(i-butoxycarbonyloxy)anthracene, 9,10-bis(n-pentyloxycarbonyloxy)anthracene, 9,10-bis(i-pentyloxycarbonyloxy)anthracene, 9,10-bis(n-hexyloxycarbonyloxy)anthracene, 9,10-bis(n-heptyloxycarbonyloxy)anthracene, and 9,10-bis(n-octyloxycarbonyloxy)anthracene.

Further, compounds which are further substituted with an alkyl group, such as 1-methyl-9,10-bis(m ethoxycarbonyloxy)anthracene, 1-methyl-9,10-bis(ethoxycarbonyloxy)anthracene, 1-methyl-9,10-bis(n-propoxycarbonyloxy)anthracene, 1-methyl-9,10-bis(i-propoxycarbonyloxy)anthracene, 1-methyl-9,10-bis(n-butoxycarbonyloxy)anthracene, 1-methyl-9,10-bis(i-butoxycarbonyloxy)anthracene, 1-methyl-9,10-bis(n-pentyloxycarbonyloxy)anthracene, 1-methyl-9,10-bis(i-pentyloxycarbonyloxy)anthracene, 1-methyl-9,10-bis(n-hexyloxycarbonyloxy)anthracene, 1-methyl-9,10-bis(n-heptyloxycarbonyloxy)anthracene, 1-methyl-9,10-bis(n-octyloxycarbonyloxy)anthracene, 2-methyl-9,10-bis(m ethoxycarbonyloxy)anthracene, 2-methyl-9,10-bis(ethoxycarbonyloxy)anthracene, 2-methyl-9,10-bis(n-propoxycarbonyloxy)anthracene, 2-methyl-9,10-bis(i-propoxycarbonyloxy)anthracene, 2-methyl-9,10-bis(n-butoxycarbonyloxy)anthracene, 2-methyl-9,10-bis(i-butoxycarbonyloxy)anthracene, 2-methyl-9,10-bis(n-pentyloxycarbonyloxy)anthracene, 2-methyl-9,10-bis(i-pentyloxycarbonyloxy)anthracene, 2-methyl-9,10-bis(n-hexyloxycarbonyloxy)anthracene, 2-methyl-9,10-bis(n-heptyloxycarbonyloxy)anthracene, 2-methyl-9,10-bis(n-octyloxycarbonyloxy)anthracene, 1-ethyl-9,10-bis(methoxycarbonyloxy)anthracene, 1-ethyl-9,10-bis(ethoxycarbonyloxy)anthracene, 1-ethyl-9,10-bis(n-propoxycarbonyloxy)anthracene, 1-ethyl-9,10-bis(i-propoxycarbonyloxy)anthracene, 1-ethyl-9,10-bis(n-butoxycarbonyloxy)anthracene, 1-ethyl-9,10-bis(i-butoxycarbonyloxy)anthracene, 1-ethyl-9,10-bis(n-pentyloxycarbonyloxy)anthracene, 1-ethyl-9,10-bis(i-pentyloxycarbonyloxy)anthracene, 1-ethyl-9,10-bis(n-hexyloxycarbonyloxy)anthracene, 1-ethyl-9,10-bis(n-heptyloxycarbonyloxy)anthracene, 1-ethyl-9,10-bis(n-octyloxycarbonyloxy)anthracene, 2-ethyl-9,10-bis(methoxycarbonyloxy)anthracene, 2-ethyl-9,10-bis(ethoxycarbonyloxy)anthracene, 2-ethyl-9,10-bis(n-propoxycarbonyloxy)anthracene, 2-ethyl-9,10-bis(i-propoxycarbonyloxy)anthracene, 2-ethyl-9,10-bis(n-butoxycarbonyloxy)anthracene, 2-ethyl-9,10-bis(i-butoxycarbonyloxy)anthracene, 2-ethyl-9,10-bis(n-pentyloxycarbonyloxy)anthracene, 2-ethyl-9,10-bis(i-pentyloxycarbonyloxy)anthracene, 2-ethyl-9,10-bis(n-hexyloxycarbonyloxy)anthracene, 2-ethyl-9,10-bis(n-heptyloxycarbonyloxy)anthracene, and 2-ethyl-9,10-bis(n-octyloxycarbonyloxy)anthracene may be mentioned.

Further, 2,3-dimethyl-9,10-bis(m ethoxycarbonyloxy)anthracene, 2,3-dimethyl-9,10-bis(ethoxycarbonyloxy)anthracene, 2,3-dimethyl-9,10-bis(n-propoxycarbonyloxy)anthracene, 2,3-dimethyl-9,10-bis(i-propoxycarbonyloxy)anthracene, 2,3-dimethyl-9,10-bis(n-butoxycarbonyloxy)anthracene, 2,3-dimethyl-9,10-bis(i-butoxycarbonyloxy)anthracene, 2,3-dimethyl-9,10-bis(n-pentyloxycarbonyloxy)anthracene, 2,3-dimethyl-9,10-bis(i-pentyloxycarbonyloxy)anthracene, 2,3-dimethyl-9,10-bis(n-hexyloxycarbonyloxy)anthracene, 2,3-dimethyl-9,10-bis(n-heptyloxycarbonyloxy)anthracene, 2,3-dimethyl-9,10-bis(n-octyloxycarbonyloxy)anthracene, 2,6-dimethyl-9,10-bis(m ethoxycarbonyloxy)anthracene, 2,6-dimethyl-9,10-bis(ethoxycarbonyloxy)anthracene, 2,6-dimethyl-9,10-bis(n-propoxycarbonyloxy)anthracene, 2,6-dimethyl-9,10-bis(i-propoxycarbonyloxy)anthracene, 2,6-dimethyl-9,10-bis(n-butoxycarbonyloxy)anthracene, 2,6-dimethyl-9,10-bis(i-butoxycarbonyloxy)anthracene, 2,6-dimethyl-9,10-bis(n-pentyloxycarbonyloxy)anthracene, 2,6-dimethyl-9,10-bis(i-pentyloxycarbonyloxy)anthracene, 2,6-dimethyl-9,10-bis(n-hexyloxycarbonyloxy)anthracene, 2,6-dimethyl-9,10-bis(n-heptyloxycarbonyloxy)anthracene, 2,6-dimethyl-9,10-bis(n-octyloxycarbonyloxy)anthracene, 2,7-dimethyl-9,10-bis(m ethoxycarbonyloxy)anthracene, 2,7-dimethyl-9,10-bis(ethoxycarbonyloxy)anthracene, 2,7-dimethyl-9,10-bis(n-propoxycarbonyloxy)anthracene, 2,7-dimethyl-9,10-bis(i-propoxycarbonyloxy)anthracene, 2,7-dimethyl-9,10-bis(n-butoxycarbonyloxy)anthracene, 2,7-dimethyl-9,10-bis(i-butoxycarbonyloxy)anthracene, 2,7-dimethyl-9,10-bis(n-pentyloxycarbonyloxy)anthracene, 2,7-dimethyl-9,10-bis(i-pentyloxycarbonyloxy)anthracene, 2,7-dimethyl-9,10-bis(n-hexyloxycarbonyloxy)anthracene, 2,7-dimethyl-9,10-bis(n-heptyloxycarbonyloxy)anthracene, 2,7-dimethyl-9,10-bis(n-octyloxycarbonyloxy)anthracene, 1,5-dimethyl-9,10-bis(m ethoxycarbonyloxy)anthracene, 1,5-dimethyl-9,10-bis(ethoxycarbonyloxy)anthracene, 1,5-dimethyl-9,10-bis(n-propoxycarbonyloxy)anthracene, 1,5-dimethyl-9,10-bis(i-propoxycarbonyloxy)anthracene, 1,5-dimethyl-9,10-bis(n-butoxycarbonyloxy)anthracene, 1,5-dimethyl-9,10-bis(i-butoxycarbonyloxy)anthracene, 1,5-dimethyl-9,10-bis(n-pentyloxycarbonyloxy)anthracene, 1,5-dimethyl-9,10-bis(i-pentyloxycarbonyloxy)anthracene, 1,5-dimethyl-9,10-bis(n-hexyloxycarbonyloxy)anthracene, 1,5-dimethyl-9,10-bis(n-heptyloxycarbonyloxy)anthracene, and 1,5-dimethyl-9,10-bis(n-octyloxycarbonyloxy)anthracene may, for example, be mentioned.

Still further, 2,3-diethyl-9,10-bis(methoxycarbonyloxy)anthracene, 2,3-diethyl-9,10-bis(ethoxycarbonyloxy)anthracene, 2,3-diethyl-9,10-bis(n-propoxycarbonyloxy)anthracene, 2,3-diethyl-9,10-bis(i-propoxycarbonyloxy)anthracene, 2,3-diethyl-9,10-bis(n-butoxycarbonyloxy)anthracene, 2,3-diethyl-9,10-bis(i-butoxycarbonyloxy)anthracene, 2,3-diethyl-9,10-bis(n-pentyloxycarbonyloxy)anthracene, 2,3-diethyl-9,10-bis(i-pentyloxycarbonyloxy)anthracene, 2,3-diethyl-9,10-bis(n-hexyloxycarbonyloxy)anthracene, 2,3-diethyl-9,10-bis(n-heptyloxycarbonyloxy)anthracene, 2,3-diethyl-9,10-bis(n-octyloxycarbonyloxy)anthracene, 2,6-diethyl-9,10-bis(methoxycarbonyloxy)anthracene, 2,6-diethyl-9,10-bis(ethoxycarbonyloxy)anthracene, 2,6-diethyl-9,10-bis(n-propoxycarbonyloxy)anthracene, 2,6-diethyl-9,10-bis(i-propoxycarbonyloxy)anthracene, 2,6-diethyl-9,10-bis(n-butoxycarbonyloxy)anthracene, 2,6-diethyl-9,10-bis(i-butoxycarbonyloxy)anthracene, 2,6-diethyl-9,10-bis(n-pentyloxycarbonyloxy)anthracene, 2,6-diethyl-9,10-bis(i-pentyloxycarbonyloxy)anthracene, 2,6-diethyl-9,10-bis(n-hexyloxycarbonyloxy)anthracene, 2,6-diethyl-9,10-bis(n-heptyloxycarbonyloxy)anthracene, 2,6-diethyl-9,10-bis(n-octyloxycarbonyloxy)anthracene, 2,7-diethyl-9,10-bis(methoxycarbonyloxy)anthracene, 2,7-diethyl-9,10-bis(ethoxycarbonyloxy)anthracene, 2,7-diethyl-9,10-bis(n-propoxycarbonyloxy)anthracene, 2,7-diethyl-9,10-bis(i-propoxycarbonyloxy)anthracene, 2,7-diethyl-9,10-bis(n-butoxycarbonyloxy)anthracene, 2,7-diethyl-9,10-bis(i-butoxycarbonyloxy)anthracene, 2,7-diethyl-9,10-bis(n-pentyloxycarbonyloxy)anthracene, 2,7-diethyl-9,10-bis(i-pentyloxycarbonyloxy)anthracene, 2,7-diethyl-9,10-bis(n-hexyloxycarbonyloxy)anthracene, 2,7-diethyl-9,10-bis(n-heptyloxycarbonyloxy)anthracene, 2,7-diethyl-9,10-bis(n-octyloxycarbonyloxy)anthracene, 1,5-diethyl-9,10-bis(methoxycarbonyloxy)anthracene, 1,5-diethyl-9,10-bis(ethoxycarbonyloxy)

anthracene, 1,5-diethyl-9,10-bis(n-propoxycarbonyloxy)
anthracene, 1,5-diethyl-9,10-bis(i-propoxycarbonyloxy)
anthracene, 1,5-diethyl-9,10-bis(n-butoxycarbonyloxy)
anthracene, 1,5-diethyl-9,10-bis(i-butoxycarbonyloxy)
anthracene, 1,5-diethyl-9,10-bis(n-pentyloxycarbonyloxy)
anthracene, 1,5-diethyl-9,10-bis(i-pentyloxycarbonyloxy)
anthracene, 1,5-diethyl-9,10-bis(n-hexyloxycarbonyloxy)
anthracene, 1,5-diethyl-9,10-bis(n-heptyloxycarbonyloxy)
anthracene, and 1,5-diethyl-9,10-bis(n-octyloxycarbonyloxy)anthracene may, for example, be mentioned.

(Method for Producing Compound having Polycyclic Aromatic Skeleton Represented by the Formula (4))

The compound having a polycyclic aromatic skeleton represented by the formula (4), for example, in the case of an anthracene compound, a 9,10-dialkoxyanthracene compound wherein each of $R^1$ and $R^2$ is a $C_{1-10}$ alkyl group, an alkoxymethyl group having a $C_{1-5}$ alkoxy group, or a $C_{6-10}$ aryl group, may be produced, for example, by the method disclosed in JP-A-2003-104925, that is, by reacting an etherifying agent with a 9,10-dihydroxyanthracene compound corresponding to the 9,10-dialkoxyanthracene compound represented by the formula (2). Further, a 9,10-bis (substituted acyloxy)anthracene compound which is the compound having a polycyclic aromatic skeleton represented by the formula (2) wherein each of $R^1$ and $R^2$ is an alkylcarbonyl group having a $C_{1-10}$ alkyl group or an arylcarbonyl group having a $C_{6-20}$ aryl group may be produced, for example, by the method disclosed in JP-A-2014-101442, that is, by reacting an acylating agent with a 9,10-dihydroxyanthracene compound corresponding to the 9,10-bis(substituted acyloxy)anthracene compound represented by the formula (2) in the presence of a basic compound. And, a 9,10-bis(substituted carbonyloxy)anthracene compound wherein each of $R^1$ and $R^2$ is an alkyloxycarbonyl group having a $C_{1-10}$ alkyl group or an aryloxycarbonyl group having a $C_{6-20}$ aryl group may be obtained, for example, by reacting a carbonic acid esterifying agent with a 9,10-dihydroxyanthracene compound corresponding to the 9,10-bis(substituted carbonyloxy)anthracene compound in the presence of a basic compound as disclosed in JP-A-2011-42743 or JP-A-2014-70203.

After completion of the reaction, as the case requires, unreacted raw material, the solvent and the catalyst may be removed by washing, by vacuum distillation, by filtration or the like alone or in combination, or the product may be isolated and purified by column chromatography. In a case where the product is a solid and crystals precipitate during the concentration, crystals may be recrystallized from a poor solvent such as an alcohol or hexane, or the crystals may be dried up as they are. In a case where the product is a liquid, it is dried up as it is, followed by purification e.g. by distillation as the case requires. Otherwise, the product may be used without purification of isolation to form an endoperoxide.

Now, the compound having a polycyclic aromatic skeleton represented by the following formula (6) which is a raw material of the compound of the formula (5) will be described. The compound of the formula (6) wherein R is an alkyloxycarbonylmethyl group having a $C_{1-12}$ alkyl group or an aryloxycarbonylmethyl group having a $C_{6-12}$ aryl group is the compound of the formula (6).

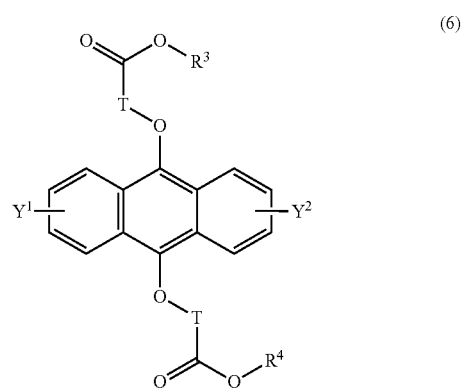

wherein T is a $C_{1-20}$ alkylene group, which may be branched by an alkyl group, each of $R^3$ and $R^4$ is a $C_{1-20}$ alkyl group, and each of $Y^1$ and $Y^2$ is a hydrogen atom, a $C_{1-8}$ alkyl group or a halogen atom.

Specific examples of $R^3$, $R^4$, T, $Y^1$ and $Y^2$ in the formula (6) are the same as the specific examples of $R^3$, $R^4$, T, $Y^1$ and $Y^2$ described for the formula (5).

Now, specific examples of the compound having a polycyclic aromatic skeleton represented by the formula (6) of the present invention will be described. Specific examples include 9,10-bis(methoxycarbonylmethyleneoxy)anthracene, 9,10-bis(ethoxycarbonylmethyleneoxy)anthracene, 9,10-bis(isopropoxycarbonylmethyleneoxy)anthracene, 9,10-bis(tert-butoxycarbonylmethyleneoxy)anthracene, 9,10-bis(n-butoxycarbonylmethyleneoxy)anthracene, 9,10-bis(methoxycarbonylpropyleneoxy)anthracene, 9,10-bis(ethoxycarbonylpropyleneoxy)anthracene, 9,10-bis(isopropoxycarbonylpropyleneoxy)anthracene, 9,10-bis(tert-butoxycarbonylpropyleneoxy)anthracene, 9,10-bis(n-butoxycarbonylpropyleneoxy)anthracene, 9,10-bis(methoxycarbonylmethylmethyleneoxy)anthracene, 9,10-bis(ethoxycarbonylmethylmethyleneoxy)anthracene, 9,10-bis(ethoxycarbonylethylmethyleneoxy)anthracene, 9,10-bis(isopropoxycarbonylmethylmethyleneoxy)anthracene, 9,10-bis(tert-butoxycarbonylmethylmethyleneoxy)anthracene, 9,10-bis(n-butoxycarbonylmethylmethyleneoxy)anthracene, 9,10-bis(methoxycarbonylbutyleneoxy)anthracene, 9,10-bis(ethoxycarbonylbutyleneoxy)anthracene, 9,10-bis(isopropoxycarbonylbutyleneoxy)anthracene, 9,10-bis(tert-butoxycarbonylbutyleneoxy)anthracene, and 9,10-bis(n-butoxycarbonylbutyleneoxy)anthracene.

Further, 9,10-bis(methoxycarbonylpentyleneoxy)anthracene, 9,10-bis(ethoxycarbonylpentyleneoxy)anthracene, 9,10-bis(isopropoxycarbonylpentyleneoxy)anthracene, 9,10-bis(tert-butoxycarbonylpentyleneoxy)anthracene, 9,10-bis(n-butoxycarbonylpentyleneoxy)anthracene, 9,10-bis(methoxycarbonylhexyleneoxy)anthracene, 9,10-bis(ethoxycarbonylhexyleneoxy)anthracene, 9,10-bis(isopropoxycarbonylhexyleneoxy)anthracene, 9,10-bis(tert-butoxycarbonylhexyleneoxy)anthracene, 9,10-bis(n-butoxycarbonylhexyleneoxy)anthracene, 9,10-bis(methoxycarbonylheptyleneoxy)anthracene, 9,10-bis(ethoxycarbonylheptyleneoxy)anthracene, 9,10-bis(isopropoxycarbonylheptyleneoxy)anthracene, 9,10-bis(tert-butoxycarbonylheptyleneoxy)anthracene, 9,10-bis(n-butoxycarbonylheptyleneoxy)anthracene, 9,10-bis(methoxycarbonyloctyleneoxy)anthracene, 9,10-bis(ethoxycarbonyloctyleneoxy)anthracene, 9,10-bis(isopropoxycarbonyloctyleneoxy)anthracene, 9,10-bis(tert-butoxycarbonyloctyleneoxy)anthracene, 9,10-bis(n- butoxycarbonyloctyleneoxy)anthracene, 9,10-bis(methoxycarbonylnonyleneoxy)anthracene, 9,10-bis(ethoxycarbonylnonyleneoxy)anthracene, 9,10-bis(isopropoxycarbonylnonyleneoxy)anthracene, 9,10-bis(tert-butoxycarbonylnonyleneoxy)anthracene, 9,10-bis(n-butoxycarbonylnonyleneoxy)anthracene, 9,10-bis(methoxycarbonyldecyleneoxy)anthracene, 9,10-bis(ethoxycarbonyldecyleneoxy)anthracene, 9,10-bis(isopropoxycarbonyldecyleneoxy)anthracene, 9,10-bis(tert-butoxycarbonyldecyleneoxy)anthracene, 9,10-bis(n-butoxycarbonyldecyleneoxy)anthracene, 9,10-bis(methoxycarbonylundecyleneoxy)anthracene, 9,10-bis(ethoxycarbonylundecyleneoxy)anthracene, 9,10-bis(isopropoxycarbonylundecyleneoxy)anthracene, 9,10-bis(tert-butoxycarbonylundecyleneoxy)anthracene, 9,10-bis(n-butoxycarbonylundecyleneoxy)anthracene, 9,10-bis(methoxycarbonyldodecyleneoxy)anthracene, 9,10-bis(ethoxycarbonyldodecyleneoxy)anthracene, 9,10-bis(isopropoxycarbonyldodecyleneoxy)anthracene, 9,10-bis(tert-butoxycarbonyldodecyleneoxy)anthracene, 9,10-bis(n-butoxycarbonyldodecyleneoxy)anthracene, 9,10-bis(methoxycarbonyltridecyleneoxy)anthracene, 9,10-bis(ethoxycarbonyltridecyleneoxy)anthracene, 9,10-bis(isopropoxycarbonyltridecyleneoxy)anthracene, 9,10-bis(tert-butoxycarbonyltridecyleneoxy)anthracene, 9,10-bis(n-butoxycarbonyltridecyleneoxy)anthracene, 9,10-bis(methoxycarbonyltetradecyleneoxy)anthracene, 9,10-bis(ethoxycarbonyltetradecyleneoxy)anthracene, 9,10-bis(isopropoxycarbonyltetradecyleneoxy)anthracene, 9,10-bis(tert-butoxycarbonyltetradecyleneoxy)anthracene, 9,10-bis(n-butoxycarbonyltetradecyleneoxy)anthracene, 9,10-bis(methoxycarbonylpentadecyleneoxy)anthracene, 9,10-bis(ethoxycarbonylpentadecyleneoxy)anthracene, 9,10-bis(isopropoxycarbonylpentadecyleneoxy)anthracene, 9,10-bis(tert-butoxycarbonylpentadecyleneoxy)anthracene, 9,10-bis(n-butoxycarbonylpentadecyleneoxy)anthracene, 9,10-bis(methoxycarbonylhexadecyleneoxy)anthracene, 9,10-bis(ethoxycarbonylhexadecyleneoxy)anthracene, 9,10-bis(isopropoxycarbonylhexadecyleneoxy)anthracene, 9,10-bis(tert-butoxycarbonylhexadecyleneoxy)anthracene, 9,10-bis(n-butoxycarbonylhexadecyleneoxy)anthracene, 9,10-bis(methoxycarbonylheptadecyleneoxy)anthracene, 9,10-bis(ethoxycarbonylheptadecyleneoxy)anthracene, 9,10-bis(isopropoxycarbonylheptadecyleneoxy)anthracene, 9,10-bis(tert-butoxycarbonylheptadecyleneoxy)anthracene, 9,10-bis(n-butoxycarbonylheptadecyleneoxy)anthracene, 9,10-bis(methoxycarbonyloctadecyleneoxy)anthracene, 9,10-bis(ethoxycarbonyloctadecyleneoxy)anthracene, 9,10-bis(isopropoxycarbonyloctadecyleneoxy)anthracene, 9,10-bis(tert-butoxycarbonyloctadecyleneoxy)anthracene, 9,10-bis(n-butoxycarbonyloctadecyleneoxy)anthracene, 9,10-bis(methoxycarbonylnonadecyleneoxy)anthracene, 9,10-bis(ethoxycarbonylnonadecyleneoxy)anthracene, 9,10-bis(isopropoxycarbonylnonadecyleneoxy)anthracene, 9,10-bis(tert-butoxycarbonylnonadecyleneoxy)anthracene, 9,10-bis(n-butoxycarbonylnonadecyleneoxy)anthracene, 9,10-bis(methoxycarbonyleicosyleneoxy)anthracene, 9,10-bis(ethoxycarbonyleicosyleneoxy)anthracene, 9,10-bis(isopropoxycarbonyleicosyleneoxy)anthracene, 9,10-bis(tert-butoxycarbonyleicosyleneoxy)anthracene, and 9,10-bis(n-butoxycarbonyleicosyleneoxy)anthracene may, for example, be mentioned.

Further, specific examples of the compound wherein each of $Y^1$ and $Y^2$ is an alkyl group include 2-ethyl-9,10-bis(methoxycarbonylmethyleneoxy)anthracene, 2-ethyl-9,10-bis(ethoxycarbonylmethyleneoxy)anthracene, 2-ethyl-9,10-bis(isopropoxycarbonylmethyleneoxy)anthracene, 2-ethyl-9,10-bis(tert-butoxycarbonylmethyleneoxy)anthracene, 2-ethyl-9,10-bis(n-butoxycarbonylmethyleneoxy)anthracene, 2-ethyl-9,10-bis(methoxycarbonylpropyleneoxy)anthracene, 2-ethyl-9,10-bis(ethoxycarbonylpropyleneoxy)anthracene, 2-ethyl-9,10-bis(isopropoxycarbonylpropyleneoxy)anthracene, 2-ethyl-9,10-bis(tert-butoxycarbonylpropyleneoxy)anthracene, and 2-ethyl-9,10-bis(n-butoxycarbonylpropyleneoxy)anthracene.

Still further, 2-amyl-9,10-bis(methoxycarbonylmethyleneoxy)anthracene, 2-amyl-9,10-bis(ethoxycarbonylmethyleneoxy)anthracene, 2-amyl-9,10-bis(isopropoxycarbonylmethyleneoxy)anthracene, 2-amyl-9,10-bis(tert-butoxycarbonylmethyleneoxy)anthracene, 2-amyl-9,10-bis(n-butoxycarbonylmethyleneoxy)anthracene, 2-amyl-9,10-bis(methoxycarbonylpropyleneoxy)anthracene, 2-amyl-9,10-bis(ethoxycarbonylpropyleneoxy)anthracene, 2-amyl-9,10-bis(isopropoxycarbonylpropyleneoxy)anthracene, 2-amyl-9,10-bis(tert-butoxycarbonylpropyleneoxy)anthracene, and 2-amyl-9,10-bis(n-butoxycarbonylpropyleneoxy)anthracene may, for example, be mentioned.

Further, specific examples of the compound wherein $Y^1$ or $Y^2$ is a halogen atom include 2-chloro-9,10-bis(methoxycarbonylmethyleneoxy)anthracene, 2-chloro-9,10-bis(ethoxycarbonylmethyleneoxy)anthracene, 2-chloro-9,10-bis(isopropoxycarbonylmethyleneoxy)anthracene, 2-chloro-9,10-bis(tert-butoxycarbonylmethyleneoxy)anthracene, 2-chloro-9,10-bis(n-butoxycarbonylmethyleneoxy)anthracene, 2-chloro-9,10-bis(methoxycarbonylpropyleneoxy)anthracene, 2-chloro-9,10-bis(ethoxycarbonylpropyleneoxy)anthracene, 2-chloro-9,10-bis(isopropoxycarbonylpropyleneoxy)anthracene, 2-chloro-9,10-bis(tert-butoxycarbonylpropyleneoxy)anthracene, and 2-chloro-9,10-bis(n-butoxycarbonylpropyleneoxy)anthracene.

(Method for Producing Compound having Polycyclic Aromatic Skeleton Represented by the Formula (6))

The compound having a polycyclic aromatic skeleton represented by the formula (6) may be obtained by reacting the corresponding 9,10-dihydroxyanthracene compound represented by the following formula (7) with a halogenated ester compound such as methyl chloroacetate, ethyl chloroacetate, n-propyl chloroacetate, isopropyl chloroacetate, n-butyl chloroacetate, methyl bromoacetate, ethyl bromoacetate, n-propyl bromoacetate, isopropyl bromoacetate, n-butyl bromoacetate, tert-butyl bromoacetate, methyl 2-bromopropionate or ethyl 4-bromobutyrate in the presence of a basic compound.

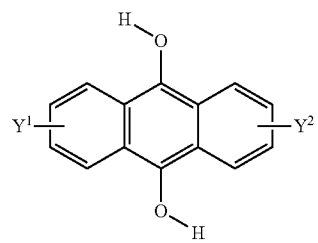

(7)

wherein each of $Y^1$ and $Y^2$ is a hydrogen atom, a $C_{1-8}$ alkyl group or a halogen atom.

The amount of the halogenated ester compound used is preferably at least 2.0 molar times and less than 10.0 molar times, more preferably at least 2.2 molar times and less than 5.0 molar times the 9,10-dihydroxyanthracene compound. If it is less than 2.0 molar times, the reaction will not be completed, and if it is at least 10.0 molar times, a side reaction will occur, thus lowering the yield and the purity.

The basic compound used may, for example, be sodium hydroxide, potassium hydroxide, sodium hydride, potassium hydride, lithium hexamethyldisilazide, lithium diisopropylamide, triethylamine, tributylamine, trihexylamine, dimethylamine, diethylamine, dipropylamine, dibutylamine, cyclohexylamine, dimethylaniline, pyridine, 4,4-dimethylaminopyridine, piperidine, γ-picoline or lutidine.

The amount of the basic compound added is preferably at least 2.0 molar times and less than 10.0 molar times, more preferably at least 2.2 molar times and less than 5.0 molar times the 9,10-dihydroxyanthracene compound. If it is less than 2.0 molar times, the reaction will not be completed, and if it is at least 10.0 molar times, a side reaction will occur, thus lowering the yield and the purity.

The reaction is carried out in a solvent or without a solvent. The solvent used is not particularly limited so long as it does not react with the ester compound used and may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, a halogenated hydrocarbon solvent such as methylene chloride, ethylene dichloride or chlorobenzene, or an alcohol solvent such as methanol, ethanol or 1-propanol.

In a case where the 9,10-dihydroxyanthracene compound is dissolved in an aqueous solution of an inorganic base and is reacted with the ester, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate tends to be low, and if it is at least 1.0 molar times, purity of the product tends to be low.

The reaction temperature is usually at least 0° C. and at most 200° C., preferably at least 10° C. and at most 100° C. If it is less than 0° C., the reaction will take too long, and if the reaction temperature is higher than 100° C., impurities tend to be large, and the purity of the desired compound will be low.

The reaction time varies depending upon the reaction temperature and is usually from about 1 hour to about 20 hours, preferably from 2 hours to 10 hours.

After completion of the reaction, as the case requires, unreacted raw material, the solvent and the catalyst may be removed by washing, by vacuum distillation, by filtration or the like alone or in combination, or the product may be isolated and purified by column chromatography. In a case where the product is a solid, crystals precipitate during the reaction, which is subjected to solid-liquid separation by filtration, followed by recrystallization from a poor solvent such as an alcohol or hexane as the case requires, or the crystals may be dried up as they are. In a case where the product is a liquid, it is dried up as it is, followed by purification e.g. by distillation as the case requires, to obtain the compound having a polycyclic aromatic skeleton represented by the formula (6).

In the reaction of singlet oxygen and the compound having a polycyclic aromatic skeleton, it is known that the ring of the compound having a polycyclic aromatic skeleton behaves as a diene, and the compound reacts with singlet oxygen at 1,4-positions of at 9,10-positions to form an endoperoxide. And, singlet oxygen that behaves electrophilically is highly reactive with a base rich in electrons. Accordingly, the aromatic ring of the compound having a polycyclic aromatic skeleton used as the reaction raw material is preferably substituted with an electron-donating group, and preferably has the electron-donating group on the ring which is the reaction site. In this meaning, the compound having a polycyclic aromatic skeleton substituted with an alkoxy group of the present invention, which is highly reactive with singlet oxygen, is preferred to a compound having an anthracene ring substituted with an alkyl group.

(Method for Producing Endoperoxide Compound Having Polycyclic Aromatic Skeleton)

The endoperoxide compound having a polycyclic aromatic skeleton represented by the formula (1), (3) or (5) of the present invention may be produced by reacting the respective corresponding compound having a polycyclic aromatic skeleton represented by the formula (2), (4) or (6) with molecular oxygen under irradiation with light having a peak wavelength within a range of from 300 nm to 410 nm.

The compound having a polycyclic aromatic skeleton represented by the formula (2), (4) or (6) of the present invention is for example dissolved in a solvent, and the solution is irradiated with light having a peak wavelength within a range of from 300 nm to 410 nm so that the compound is reacted with oxygen dissolved in the solution, whereby the corresponding endoperoxide compound having a polycyclic aromatic skeleton represented by the formula (1), (3) or (5) may be produced.

The reaction solvent is not particularly limited so long as the compound having a polycyclic aromatic skeleton is soluble in it and it does not react with the formed endoperoxide, and may, for example, be a ketone solvent such as acetone or methyl isobutyl ketone, an ether solvent such as tetrahydrofuran, a halogenated hydrocarbon such as methylene chloride, an organic acid ester solvent such as ethyl acetate or butyl acetate, an amide solvent such as N,N-dimethylformamide, or an aromatic hydrocarbon solvent such as benzene or toluene.

Further, in a case where subsequent to formation the endoperoxide, the endoperoxide is used as the radical polymerization initiator, the radical polymerizable compound may be used as the solvent. As the radical polymerizable compound which may be used in the present invention, styrene, methylstyrene, divinylbenzene, p-hydroxystyrene, vinyl acetate, (meth)acrylic acid, acrylonitrile, methacrylonitrile, acrylamide, a (meth)acrylic acid ester or a fumaric acid ester, or an oligomer thereof may, for example, be mentioned.

The reaction concentration depends on the solvent used and/or the radical polymerizable compound, and to 100 parts by weight of the solvent and/or the radical polymerizable compound, the compound having a polycyclic aromatic skeleton is added in an amount of from 0.01 part by weight to 10 parts by weight, preferably from 0.05 part by weight to 5 parts by weight, more preferably from 0.1 parts by weight to 3 parts by weight.

The reaction temperature depends on the endoperoxide compound having a polycyclic aromatic skeleton used, but the reaction is carried out in a temperature range of from −20° C. to 150° C., preferably from 0° C. to 120° C.

The compound having a polycyclic aromatic skeleton dissolved in the solvent is irradiated with light having a peak wavelength within a range of from 300 nm to 410 nm with stirring. On that occasion, oxygen or air may be blown in the solution. Otherwise, the solution may be formed into a thin film, which is irradiated with light to increase the contact efficiency with oxygen on the surface of the solution so that the reaction proceeds without stirring or air blowing.

The intensity of the light having a peak wavelength within a range of from 300 nm to 410 nm is from about 1 to about 2,000 mW/cm$^2$. The irradiation time depends on the light intensity and is from about 0.1 second to about 120 minutes.

The irradiation source which applies the light having a peak wavelength within a range of from 300 nm to 410 nm is preferably an ultraviolet LED with a center wavelength of 405 nm, an ultraviolet LED with a center wavelength of 395 nm, an ultraviolet LED with a center wavelength of 385 nm, an ultraviolet LED with a center wavelength of 375 nm, or an ultraviolet LED with a center wavelength of 365 nm, but any lamp having an emission spectrum within a wavelength range of from 300 nm to 410 nm may be used, and a laser, an electrodeless lamp such as Fusion D-bulb or V-bulb, a xenon lamp, a black light lamp, an ultrahigh pressure mercury lamp, a metal halide lamp, a gallium doped lamp and the like may also be used. Further, sunlight may also be employed. In a case where the compound having a polycyclic aromatic skeleton of the present invention is an anthracene compound, preferred is a 385 nm, 395 nm or 405 nm ultraviolet LED, or a 405 nm laser, which emits light having a wavelength close to the absorption wavelength of the anthracene compound.

The mechanism how the endoperoxide compound having a polycyclic aromatic skeleton of the present invention forms is not clearly understood but is considered as follows. That is, the compound having a polycyclic aromatic skeleton functions as a singlet oxygen generator, that is, the compound having a polycyclic aromatic skeleton absorbs applied light and becomes in an excited state, and the excited state becomes an excited triplet state by intersystem crossing. The excited triplet state of the compound having a polycyclic aromatic skeleton undergoes triplet-triplet energy transfer (triplet-triplet annihilation) with triplet oxygen in the ground state, whereby the compound having a polycyclic aromatic skeleton in the ground state and singlet oxygen form. And, to the singlet oxygen formed by the reaction, the compound having a polycyclic aromatic skeleton in the ground state functions as a singlet oxygen trapper. That is, it is considered that singlet oxygen reacts with an electron-rich diene structure of the compound having a polycyclic aromatic skeleton to form the endoperoxide compound having a polycyclic aromatic skeleton.

In the reaction solution of the compound having a polycyclic aromatic skeleton, so long as the effects of the present invention are not impaired, a singlet oxygen generator other than the compound having a polycyclic aromatic skeleton may coexist for reaction. In the present invention, the compound having a polycyclic aromatic skeleton is used as a reaction reagent (singlet oxygen trapper) with singlet oxygen and at the same time functions as a singlet oxygen generator to form singlet oxygen. In this reaction, to further increase the efficiency for production of singlet oxygen, a single oxygen generator other than the compound having a polycyclic aromatic skeleton may coexist.

(Single Oxygen Generator Other than Compound having Polycyclic Aromatic Skeleton)

As the singlet oxygen generator other than the compound having a polycyclic aromatic skeleton which may coexist, rose bengal, methylene blue, Azure A, a porphyrin or metalloporphyrin (for example, zinc tetrahydroxyphenylporphyrin, zinc tetracarboxyphenylporphyrin, zinc uroporphyrin, zinc protoporphyrin, tetrasulfonatophenyl porphyrin, Zn tetrasulfonatophenyl porphyrin, tetramethylpyridinium porphyrin, Zn tetramethylpyridinium porphyrin, hematoporphyrin, Zn hematoporphyrin), a phthalocyanine and a metallophthalocyanine, a thioxanthone, or a fluorescein such as eosine Y may, for example, be mentioned.

With respect to the amount of the single oxygen generator other the compound having a polycyclic aromatic skeleton, the single oxygen generator other the compound having a polycyclic aromatic skeleton is added in an amount of from 1 part by weight to 200 parts by weight to 100 parts by weight of the compound having a polycyclic aromatic skeleton.

In a case where the singlet oxygen generator other than the compound having a polycyclic aromatic skeleton is used in combination, as the light to be used for the reaction, in addition to the light having a peak wavelength within a range of from 300 nm to 410 nm, light having a wavelength optimum for the singlet oxygen generator, for example longer wavelength light of 530 nm may also be used.

Further, the compound having a polycyclic aromatic skeleton of the present invention may be used alone or in combination of two or more. For example, the compound of the formula (2) and the compound of the formula (4) may be used in combination.

After completion of the reaction, as the case requires, the endoperoxide compound having a polycyclic aromatic skeleton formed in the solvent may be isolated and purified by removing unreacted raw material, the solvent and the catalyst by washing, by vacuum distillation, by filtration or the like alone or in combination, or by column chromatography. In a case where the product is a solid, crystals precipitate during the concentration, which may be recrystallized from a poor solvent such as an alcohol or hexane, or the crystals may be dried up as they are. In a case where the product is a liquid, it is dried up as it is, followed by purification as the case requires. Otherwise, the endoperoxide compound may be used as the radical polymerization initiator as it is without purification of isolation.

(Method (1) for Curing Radical Polymerizable Composition)

A radical polymerizable composition can be prepared by adding the endoperoxide compound having a polycyclic aromatic skeleton of the present invention, as the radical polymerization initiator, to a radical polymerizable compound.

(Photoradical Polymerization Initiator)

The endoperoxide compound having a polycyclic aromatic skeleton of the present invention is excited by irradiation with light having a wavelength in a specific range, the excited species is converted to a radical species having a capability of initiating radical polymerization of the radical polymerizable compound and functions as a photoradical polymerization initiator to initiate radical polymerization of the radical polymerizable compound.

(Heat Radical Polymerization Initiator)

Further, the endoperoxide compound having a polycyclic aromatic skeleton of the present invention functions as a heat radical polymerization initiator which is decomposed by heat to generate a radical species and initiate radical polymerization of the radical polymerizable compound.

(Radical Polymerizable Compound)

The radical polymerizable compound which may be used in the present invention may, for example, be styrene, methylstyrene, divinylbenzene, p-hydroxystyrene, vinyl acetate, (meth)acrylic acid, acrylonitrile, methacrylonitrile, acrylamide, a (meth)acrylic acid ester or a fumaric acid ester, or an oligomer thereof.

Specific examples of the (meth)acrylic acid ester include methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, isoamyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, isooctyl (meth)acrylate, nonyl (meth)acrylate, adamantyl (meth)acrylate, 3-hydroxy-1-adamantyl (meth)acrylate, 1-methyladamantyl (meth)acrylate, 1-ethyladamantyl (meth)acrylate, 3,5-dihydroxy-1-adamantyl (meth)acrylate, benzyl (meth)acrylate, 2-methoxyethyl (meth)acrylate, 2-butoxyethyl (meth)acrylate, 2-ethoxyethyl (meth)acrylate, 3-methoxypropyl (meth)acrylate, 3-methoxybutyl (meth)acrylate, phenoxyethyl (meth)acrylate, methylphenoxyethyl (meth)acrylate, m-phenoxybenzyl (meth)acrylate, ethylcarbitol (meth)acrylate, methoxytriethylene glycol (meth)acrylate, ethoxydiethylene glycol (meth)acrylate, 2-hydroxy-3-phenoxypropyl (meth)acrylate, 2-ethylhexyldiethylene glycol (meth)acrylate, methoxy-dipropylene glycol (meth)acrylate, 2-hydroxyethyl (meth)acrylate, 2-hydroxypropyl (meth)acrylate, 3-hydroxypropyl (meth)acrylate, 2-hydroxybutyl (meth)acrylate, 4-hydroxybutyl (meth)acrylate, 1,4-cyclohexanedimethanol (meth)acrylate, glycerin (meth)acrylate, polyethylene glycol (meth)acrylate, polypropylene glycol (meth)acrylate, polyethylene glycol-polypropylene glycol (meth)acrylate, polyethylene glycol-polypropylene glycol (meth)acrylate, polyethylene glycol-polytetramethylene glycol (meth)acrylate, polypropylene glycol-polytetramethylene glycol (meth)acrylate, polyethylene glycol-polybutylene glycol (meth)acrylate, ethoxylated-o-phenylphenol (meth)acrylate, methoxypolyethylene glycol (meth)acrylate, phenoxypolyethylene glycol (meth)acrylate, p-cumyl phenoxyethyl (meth)acrylate, nonylphenoxypolyethylene glycol (meth)acrylate (manufactured by Hitachi Chemical Co., Ltd., FANCRYL FA-314A, FA-318A, etc.), octoxypolyethylene glycol-polypropylene glycol (meth)acrylate, lauroyloxypolyethylene glycol (meth)acrylate, stearyloxy polyethylene glycol (meth)acrylate, phenoxypolyethylene glycol-polypropylene glycol (meth)acrylate, nonylphenoxy-polyethylene glycol-polypropylene glycol (meth)acrylate, 3-chloro-2-hydroxypropyl (meth)acrylate, 2-(2-vinyloxyethoxy)ethyl (meth)acrylate, allyloxypolyethylene glycol-polypropylene glycol (meth)acrylate, undecylenoxy (meth)acrylate, undecylenoxy polyethylene glycol (meth)acrylate, tetraethylene glycol diacrylate, trimethylolpropane triacrylate, pentaerythritol triacrylate, tricyclo[5,2,1,02,6]decanedimethanol diacrylate, isobornyl methacrylate, epoxy acrylate, urethane acrylate, polyester acrylate, polybutadiene acrylate, polyol acrylate, polyether acrylate, a silicone resin acrylate, and imide acrylate.

Further, an unsaturated monomer having a bisphenol skeleton may also be mentioned. Its specific examples include ethylene oxide added bisphenol A (meth)acrylic acid ester, ethylene oxide added tetrabromobisphenol A (meth)acrylic acid ester, propylene oxide added bisphenol A (meth)acrylic acid ester, and propylene oxide added tetrabromobisphenol A (meth)acrylic acid ester. Commercial products of the unsaturated monomer having such a structure include Viscoat #700, #540 (manufactured by OSAKA ORGANIC CHEMICAL INDUSTRY LTD.), ARONIX M-208, M-210 (manufactured by TOAGOSEI CO., LTD.) and NK ESTER BPE-100, BPE-200, BPE-500, A-BPE-4 (manufactured by SHIN-NAKAMURA CHEMICAL Co., Ltd.).

The fumaric acid ester compound may, for example, be a fumaric acid monoester compound such as monomethyl fumarate, monoethyl fumarate, mono-n-propyl fumarate, di-mono-i-propyl fumarate, mono-n-butyl fumarate, mono-i-butyl fumarate, mono-t-butyl fumarate, mono-n-amyl fumarate, mono-i-amyl fumarate, mono-n-hexyl fumarate, mono-n-heptyl fumarate, mono-n-octyl fumarate or mono-2-ethylhexyl fumarate.

Further, a fumaric acid diester compound such as dimethyl fumarate, diethyl fumarate, di-n-propyl fumarate, di-i-propyl fumarate, di-n-butyl fumarate, di-i-butyl fumarate, di-t-butyl fumarate, di-n-amyl fumarate, di-i-amyl fumarate, di-n-hexyl fumarate, di-n-heptyl fumarate, di-n-octyl fumarate, bis(2-ethylhexyl) fumarate, ethyl methyl fumarate, ethyl n-propyl fumarate, ethyl i-propyl fumarate, ethyl n-butyl fumarate, ethyl i-butyl fumarate, ethyl t-butyl fumarate, ethyl n-amyl fumarate, ethyl i-amyl fumarate, ethyl n-hexyl fumarate, ethyl n-heptyl fumarate, ethyl n-octyl or ethyl (2-ethylhexyl) fumarate may also be mentioned.

Among the above radical polymerizable compounds, preferred is (meth)acrylic acid, a (meth)acrylic acid ester, a fumaric acid ester or styrene or an oligomer thereof.

In the radical polymerizable composition of the present invention, the amount of the endoperoxide compound having a polycyclic aromatic skeleton of the present invention added is, to the radical polymerizable compound, at least 0.01 wt % and less than 3.0 wt %, preferably at least 0.05 wt % and less than 1.0 wt %. If the amount added is less than 0.01 wt %, the curing rate may be low, and if the amount added is at least 3.0 wt %, physical properties of the cured product may be impaired.

(Curing Method)

The method of subjecting the radical polymerizable composition of the present invention to radical polymerization will be described.

(Photoradical Polymerization)

First, a case where the radical polymerization initiation energy is light will be described. The radical polymerizable composition of the present invention may be polymerized and cured by irradiation with light having a wavelength within a specific range.

Polymerization of the radical polymerizable composition may be conducted in the form of a film, or the composition may be cured into a block. In a case where the radical polymerizable composition is polymerized into a film, the composition is formed into a liquid form and applied on a substrate such as a polyester film or a tack film e.g. by a bar coater and irradiated with light having a wavelength within a specific range thereby to be polymerized.

(Coating)

In a case where the composition is polymerized into a film, as the substrate, a film, paper, an aluminum foil, a metal of the like is mainly used, but the substrate is not particularly limited. The material of the film as the substrate may, for example, be polyester, triacetyl cellulose (TAC) or polyvinyl alcohol (PVA). The substrate film is usually one having a film thickness of less than 100 μm. The bar coater used to adjust the film thickness of the coating film obtainable by applying the radical polymerizable composition is not particularly limited, but a bar coater capable of adjusting the film thickness to be at least 1 μm and less than 100 μm is used. Further, by spin coating method or screen printing method, the composition may be applied into a smaller film thickness or a larger film thickness.

(Irradiation Source)

The coating film formed of the radical polymerizable composition thus formed is irradiated with energy rays including light having a wavelength within a range of from 230 nm to 330 nm at an intensity of form about 1 to about 2,000 mW/cm$^2$ thereby to obtain a photocured product. The irradiation source used may be any one which can apply light having a wavelength within a range of from 230 nm to 330 nm. For example, a high pressure mercury lamp, a low pressure mercury lamp, an excimer lamp or a deep UV lamp may be used.

The temperature at the time of irradiating the radical polymerizable composition of the present invention with light energy may be room temperature, however, since the endoperoxide compound having a polycyclic aromatic skeleton of the present invention functions also as the heat radical polymerization initiator, it is effective to warm the radical polymerizable composition. In a case where the composition is warmed, the temperature is preferably from 30° C. to 150° C., particularly preferably from 50° C. to 130° C. By warming the radical polymerizable composition, decomposition of the endoperoxide compound having a polycyclic aromatic skeleton is promoted, and its curing can be accelerated.

As the heat treatment, heating by a hot plate or the like may be employed, or a halogen heater or a hot air heater may be used.

Irradiation with infrared rays may be employed together with the heat treatment or instead of the heat treatment. The infrared rays applied may be either near infrared rays or far infrared rays. Irradiation with infrared rays is preferred to external heating in that decomposition of the peroxide in the inside efficiently takes place. Further, a microwave heating apparatus which utilizes frictional heat generated by vibration of constituting molecules in the system caused by microwave irradiation may also be used. The frequency is mainly 2.45 GHz or 915 MHz.

Further, in the radical polymerizable composition of the present invention, so long as the effects of the present invention are not impaired, a photoradical polymerization sensitizer to promote decomposition of the formed peroxide and to accelerate curing, may further be added. The photoradical polymerization sensitizer is a compound having such effects that the photoradical polymerization sensitizer is excited by the light applied, and the excitation energy is transferred to the endoperoxide compound having a polycyclic aromatic skeleton, thereby to accelerate decomposition of the endoperoxide compound having a polycyclic aromatic skeleton. As the photoradical polymerization sensitizer, e.g. a thioxanthone compound may be used. Further, the compound having a polycyclic aromatic skeleton which is the raw material of the endoperoxide compound having a polycyclic aromatic skeleton of the present invention may be used. Further, the compound having a polycyclic aromatic skeleton remaining unreacted in production of the endoperoxide compound having a polycyclic aromatic skeleton may be used, as the photoradical polymerization sensitizer, as it is without being isolated.

The thioxanthone which may be added may, for example, be thioxanthone, 2-chlorothioxanthone, 2,4-diethylthioxanthone or 2,4-diisopropylthioxanthone.

In a case where the compound having a polycyclic aromatic skeleton which is the raw material of the endoperoxide compound having a polycyclic aromatic skeleton of the present invention is used as the photoradical polymerization sensitizer, the compound having a polycyclic aromatic skeleton of the formula (6) is particularly preferred. The compound having a polycyclic aromatic skeleton of the formula (6) is less likely to cause migration or blooming at the time of curing the radical polymerizable composition or during storage of the cured product, and is thereby less likely to cause dusting and coloring of the cured product, probably due to a specific ester group structure in its structure, as compared with the compound having a polycyclic aromatic skeleton of the formula (4) and the thioxanthone compound.

Depending upon the photoradical polymerization sensitizer used, the wavelength of the light applied to cure the radical polymerizable composition may be fitted to the absorption wavelength of the photoradical polymerization sensitizer. Further, lights differing in the wavelength, that is light with an absorption wavelength of the photoradical polymerization sensitizer and light having a wavelength of from 230 nm to 330 nm may be applied. For example, in a case where the compound having a polycyclic aromatic skeleton of the present invention or the thioxanthone compound is used, as the absorption wavelength of the photoradical polymerization sensitizer, a wavelength of from 300 nm to 410 nm is employed. As an irradiation source used, preferred is an ultraviolet LED with a center wavelength of 405 nm, an ultraviolet LED with a center wavelength of 395 nm, an ultraviolet LED with a center wavelength of 385 nm, an ultraviolet LED with a center wavelength of 375 nm, or an ultraviolet LED with a center wavelength of 365 nm, but any lamp having an emission spectrum within a wavelength range of from 300 nm to 410 nm may be used, and an electrodeless lamp such as Fusion D-bulb or V-bulb, a xenon lamp, a black light lamp, an ultrahigh pressure mercury lamp, a metal halide lamp, a gallium doped lamp, a laser and the like may also be used. Further, sunlight may also be employed. A 385 nm, 395 nm or 405 nm ultraviolet LED, or a 405 nm laser is particularly preferred.

In a case where 405 nm light is used, among the compounds of the formula (4), the compound having a polycyclic aromatic skeleton wherein each of $R^1$ and $R^2$ is a $C_{1-10}$ alkyl group, an alkoxymethyl group having a $C_{1-5}$ alkoxy group or a $C_{6-10}$ aryl group, or the compound having a polycyclic aromatic skeleton of the formula (6), which has intense ultraviolet absorption in the vicinity of 405 nm, is preferred.

Further, to promote decomposition of the endoperoxide and to accelerate curing, as a decomposition promoter, a reducing agent may be added. The reducing agent may be a transition metal such as iron or cobalt, an amine such as dimethylaniline or a phosphine such as triphenylphosphine.

(Heat Radical Polymerization)

Now, a case where the radical polymerization initiation energy is heat will be described. The radical polymerizable composition of the present invention may be polymerized and cured by being heated to a predetermined temperature.

Polymerization of the radical polymerizable composition may be conducted in the form of a film, or the composition may be cured into a block. In a case where the radical polymerizable composition is polymerized into a film, the composition is formed into a liquid form and applied on a substrate such as a polyester film or a tack film e.g. by a bar coater, in the same manner as the photoradical polymerization, and heated thereby to be polymerized.

As the heating method, heating by a hot plate or the like may be employed, or a halogen heater or a hot air heater may be used. The heating temperature is preferably from 30° C. to 150° C. In general, the endoperoxide compound having an anthracene skeleton as the polycyclic aromatic skeleton is more stable against heat than the endoperoxide compound having a naphthalene skeleton, and thereby requires a higher reaction temperature. For example, the reaction temperature is about 40° C. for an endoperoxide compound having a naphthalene skeleton, whereas the reaction temperature is at least 100° C. for an endoperoxide compound having an anthracene skeleton.

Irradiation with infrared rays may be employed together with the heat treatment or instead of the heat treatment. The infrared rays applied may be either near infrared rays or far infrared rays. Irradiation with infrared rays is preferred to external heating in that decomposition of the peroxide in the inside efficiently takes place. Further, a microwave heating apparatus which utilizes frictional heat generated by vibration of constituting molecules in the system caused by microwave irradiation may also be used. The frequency is mainly 2.45 GHz or 915 MHz.

Further, an endoperoxide decomposition promoter may be added. Such a decomposition promoter may, for example, be a transition metal such as iron or cobalt, an organic metal salt such as zinc naphthenate, cobalt naphthenate, tin octylate, cobalt octylate, cobalt(II) bisacetylacetonate or cobalt(III) trisacetylacetonate, an imidazole or its derivative, an organic phosphorus compound such as a phosphine such as triphenylphosphine or a phosphonium salt, a secondary amine such as dimethylaniline, a tertiary amine, or a quaternary ammonium salt, and they may be used alone or in combination of two or more.

The above decomposition promoter is a reducing agent, and among the reducing agents, a reducing agent with an oxidation-reduction potential of at most −0.2 V is preferred, and a transition metal with an oxidation-reduction potential of at most −0.5 V is particularly preferred. By addition of the decomposition promoter, the polymerization initiation temperature may be lowered.

(Method (2) for Curing Radical Polymerizable Composition)

Method (1) for curing the radical polymerizable composition of the present invention is, as described above, a method of adding the endoperoxide compound having a polycyclic aromatic skeleton of the present invention as the radical polymerization initiator to the radical polymerizable compound, and it is also possible to polymerize and cure the radical polymerizable compound while forming the endoperoxide compound having a polycyclic aromatic skeleton in the radical polymerizable composition.

That is, the radical polymerizable composition containing the compound having a polycyclic aromatic skeleton and the radical polymerizable compound is irradiated with ultraviolet rays in the presence of oxygen to form the endoperoxide compound having a polycyclic aromatic skeleton, and then the endoperoxide compound having a polycyclic aromatic skeleton is used as the radical polymerization initiator to conduct a radical polymerization reaction of the radical polymerizable compound.

According to this curing method, the compound having a polycyclic aromatic skeleton converts oxygen present in the system to singlet oxygen and reacts with the resulting singlet oxygen and becomes an initiator by itself, and thus the radical polymerizable composition can be polymerized even in the presence of oxygen, that is, radical polymerized without being susceptible to oxygen inhibition.

Further, in Method (2) for curing radical polymerizable composition, the compound having a polycyclic aromatic skeleton which is the raw material of the endoperoxide having a polycyclic aromatic skeleton functions also as the radical polymerization sensitizer to promote decomposition of the radical polymerization initiator and to further increase the polymerization rate.

In general, an anthracene compound is known to have a radical polymerization inhibitory effect, but the compound having a polycyclic aromatic skeleton used as the raw material in the present invention has a remarkably low radical inhibitory effect under irradiation with light, as different from anthracene, a 9,10-dialkyl anthracene compound and the like, and even when it remains in the radical polymerizable composition, it will not inhibit radical polymerization. Particularly, the compound having a polycyclic aromatic skeleton represented by the formula (6) has a remarkably low inhibitory effect and is thereby preferred.

In the curing method of the present invention, as the compound having a polycyclic aromatic skeleton, a single compound may be used, or a plurality of the compounds having a polycyclic aromatic skeleton of the present invention may be used in combination.

In Method (2), the radical polymerizable composition may be cured into a block but is preferably polymerized into a thin film or a film. The radical polymerizable composition is formed into a liquid form and applied on a substrate such as a polyester film or a tack film e.g. by a bar coater and irradiated with light having a wavelength within a specific range thereby to be polymerized. As the coating method, the same method as in Method (1) may be employed.

In Method (2), irradiation with light having a wavelength of from 300 nm to 410 nm, at which the compound having a polycyclic aromatic skeleton is excited, is necessary. The irradiation source used is preferably an ultraviolet LED with a center wavelength of 405 nm, an ultraviolet LED with a center wavelength of 395 nm, an ultraviolet LED with a center wavelength of 385 nm, an ultraviolet LED with a center wavelength of 375 nm, or an ultraviolet LED with a center wavelength of 365 nm, but any lamp having an emission spectrum within a wavelength range of from 300 nm to 410 nm may be used, and a laser, an electrodeless lamp such as Fusion D-bulb or V-bulb, a xenon lamp, a black light lamp, an ultrahigh pressure mercury lamp, a metal halide lamp, a gallium doped lamp and the like may also be used. Further, sunlight may also be employed. A 385 nm, 395 nm or 405 nm ultraviolet LED, or a 405 nm laser is particularly preferred.

(Atmosphere)

Method (2) is carried out in the presence of oxygen to form singlet oxygen. "In the presence of oxygen" means that oxygen is not positively removed, and means atmosphere not replaced with a nitrogen gas, a helium gas or the like. On the contrary, air or oxygen may be positively blown in.

Specifically, the surface of the radical polymerizable composition should be in contact with air. Otherwise, when the surface of the radical polymerizable composition is covered with a film, oxygen should be sufficiently dissolved in the radical polymerizable composition.

In Method (2), light energy and/or heat energy is employed as the energy when the formed endoperoxide compound having a polycyclic aromatic skeleton is decomposed, and in a case where light energy is used, the remaining compound having a polycyclic aromatic skeleton, such as the compound having a polycyclic aromatic skeleton used as the raw material present in excess, absorbs light energy, which is transferred to the endoperoxide compound having a polycyclic aromatic skeleton to decompose the endoperoxide compound having a polycyclic aromatic skeleton thereby to generate a radical polymerization initiation species. Accordingly, in Method (2), only light having a wavelength at which the compound having a polycyclic aromatic skeleton is excited, should be applied to polymerize and cure the radical polymerizable composition.

Accordingly, in Method (2), it is not necessary to newly add a photoradical polymerization sensitizer, however, so long as the effects of the present invention are not impaired, a photoradical polymerization sensitizer other than the compound having a polycyclic aromatic skeleton, for example a thioxanthone, may be added.

The thioxanthone which may be added may, for example, be thioxanthone, 2-chlorothioxanthone, 2,4-diethylthioxanthone or 2,4-diisopropylthioxanthone.

Further, in the radical polymerizable composition used in Method (2), so long as the effects of the present invention are not impaired, a single oxygen generator other than the compound having a polycyclic aromatic skeleton may coexist for reaction. In the present invention, the compound having a polycyclic aromatic skeleton is used as a reaction reagent (singlet oxygen trapper) with singlet oxygen and at the same time functions as the singlet oxygen generator to from singlet oxygen. In this reaction, to further increase the efficiency for production of singlet oxygen, a singlet oxygen generator other than the compound having a polycyclic aromatic skeleton may coexist.

(Singlet Oxygen Generator Other than Compound having Polycyclic Aromatic Skeleton)

The singlet oxygen generator other than the compound having a polycyclic aromatic skeleton which may coexist may, for example, be rose bengal, methylene blue, Azure A, a porphyrin or metalloporphyrin (for example, zinc tetrahydroxyphenylporphyrin, zinc tetracarboxyphenylporphyrin, zinc uroporphyrin, zinc protoporphyrin, tetrasulfonatophenyl porphyrin, Zn tetrasulfonatophenyl porphyrin, tetramethylpyridinium porphyrin, Zn tetramethylpyridinium porphyrin, hematoporphyrin, Zn hematoporphyrin), a phthalocyanine and a metallophthalocyanine, a thioxanthone, or a fluorescein such as eosine Y.

The temperature at the time of irradiating the radical polymerizable composition of the present invention with light energy may be room temperature, however, since the endoperoxide compound having a polycyclic aromatic skeleton of the present invention functions also as the heat radical polymerization initiator, it is effective to warm the radical polymerizable composition. In a case where the composition is warmed, the temperature is preferably from 30° C. to 150° C., particularly preferably from 50° C. to 130° C. By warming the radical polymerizable composition, decomposition of the endoperoxide compound having a polycyclic aromatic skeleton is promoted, and its curing can be accelerated.

As the heat treatment, heating by a hot plate or the like may be employed, or a halogen heater or a hot air heater may be used.

Irradiation with infrared rays may be employed together with the heat treatment or instead of the heat treatment. The infrared rays applied may be either near infrared rays or far infrared rays. Irradiation with infrared rays is preferred to external heating in that decomposition of the peroxide in the inside efficiently takes place. Further, a microwave heating apparatus which utilizes frictional heat generated by vibration of constituting molecules in the system caused by microwave irradiation may also be used. The frequency is mainly 2.45 GHz or 915 MHz.

Further, an endoperoxide decomposition promoter may be added. Such a decomposition promoter may, for example, be a transition metal such as iron or cobalt, an organic metal salt such as zinc naphthenate, cobalt naphthenate, tin octylate, cobalt octylate, cobalt(II) bisacetylacetonate or cobalt(III) trisacetylacetonate, an imidazole or its derivative, an organic phosphorus compound such as a phosphine such as triphenylphosphine or a phosphonium salt, a secondary amine such as dimethylaniline, a tertiary amine, or a quaternary ammonium salt, and they may be used alone or in combination of two or more.

The above decomposition promoter is a reducing agent, and among the reducing agents, a reducing agent with an oxidation-reduction potential of at most −0.2 V is preferred, and a transition metal with an oxidation-reduction potential of at most −0.5 V is particularly preferred.

Further, Methods (1) and (2) in the present invention are characterized in that polymerization proceeds even without using a conventional photoradical polymerization initiator commonly used, and so long as the effects of the present invention are not impaired, a conventional photoradical polymerization initiator commonly used may be used in combination. Method (2) of the present invention is characterized in that no oxygen inhibition occurs even when a commonly used photoradical polymerization initiator is used, since oxygen is excited to singlet oxygen.

The conventional photoradical polymerization initiator commonly used may, for example, be a benzoin compound, an acetophenone, a benzophenone, a thioxanthone, an α-acyloxime ester, a phenylglyoxylate, a benzyl, an azo compound, a diphenyl sulfide compound, an acylphosphine oxide compound, an organic dye compound, iron-phthalocyanine, a benzoin, a benzoin ether or an anthraquinone. Specifically, it may, for example, be a benzoin such as benzoin, benzoin methyl ether, benzoin ethyl ether, benzoin propyl ether or benzoin isobutyl ether; an acetophenone such as acetophenone, 2,2-diethoxy-2-phenylacetophenone, 1,1-dichloroacetophenone, 2-hydroxy-2-methyl-phenylpropan-1-one, diethoxyacetophenone, 1-hydroxycyclohexyl phenyl ketone or 2-methyl-1-[4-(methylthio)phenyl]-2-morpholinopropan-1-one; an anthraquinone such as 2-ethylanthraquinone, 2-t-butylanthraquinone, 2-chloroanthraquinone or 2-amylanthraquinone; a thioxanthone such as 2,4-diethylthioxanthone, 2-isopropylthioxanthone or 2-chlorothioxanthone; a ketal such as acetophenone dimethyl ketal or benzyl dimethyl ketal; a benzophenone such as benzophenone, 4-benzoyl-4'-methyl diphenyl sulfide or 4,4'-bismethylaminobenzophenone; or a phosphine oxide such as 2,4,6-trimethylbenzoyl diphenylphosphine oxide or bis(2,4,6-trimethylbenzoyl)-phenylphosphine oxide. The photoradical polymerization initiators disclosed in known literature, for example, Journal of Synthetic Organic Chemistry, Japan, 66, 458 (2008) may be mentioned.

Further, an acylphosphine oxide compound such as 1-hydroxycyclohexyl phenyl ketone (Irgacure 184 manufactured by BASF, Irgacure is registered trademark of BASF), (2-methyl-1-(4-(methylthio)phenyl)-2-(4-morpholinyl)-1-propanone) (Irgacure 907) or bis(2,4,6-trimethylbenzoyl)-diphenylphosphine oxide (Irgacure 819); a titanocene compound such as bis($\eta^5$-2,4-cyclopentadien-1-yl)-bis(2,6-difluoro-3-(1H-pyrrol-1-yl)-phenyl) titanium (Irgacure 784); or a naphthacenequinone compound such as 6,12-bis (trimethylsilyloxy)-1,11-naphthacenequinone.

Still further, an onium salt photoradical polymerization initiator may also be used. The onium salt photoradical polymerization initiator is used usually as a photocationic polymerization initiator which generates a cationic species when irradiated with light, and it was found that when added to the radical polymerizable composition of the present invention, it functions as the photoradical polymerization initiator. The onium salt photoradical polymerization initiator may, for example, be a sulfonium salt, an iodonium salt, a pyridinium salt or a phosphonium salt, and in view of sensitivity to light applied, it is preferably a sulfonium salt or an iodonium salt.

The sulfonium salt may be a diphenylalkyl sulfonium sat, a dinaphthylalkyl sulfonium salt or a triphenyl sulfonium salt, and in view of sensitivity to light applied, it is preferably a triphenyl sulfonium salt. The triphenyl sulfonium salt may, for example, be S,S,S',S'-tetraphenyl-S,S'-(4, 4'-thiodiphenyl)disulfonium bishexafluorophosphate, diphenyl-4-phenylthiophenylsulfonium hexafluorophosphate or triphenylsulfonium hexafluorophosphate and is available, for example, as UVI-6992 manufactured by The Dow Chemical Company (compound name: S,S,S',S'-tetraphenyl-S,S'-(4, 4'-thiodiphenyl)disulfonium bishexafluorophosphate).

Further, the iodonium salt may, for example, be a diphenyl iodonium salt, a phenyl naphthyl iodonium salt or a dinaphthyl iodonium salt, and in view of sensitivity to light applied, it is preferably a diphenyl iodonium salt. The diphenyl iodonium salt may, for example, be 4-isobutylphenyl-4'-methylphenyliodonium hexafluorophosphate, bis(dodecylphenyl)iodonium hexafluoroantimonate or 4-isopropylphenyl-4'-methylpheyliodonium tetrakispentafluorophenylborate, and is available, for example, as Irgaure 250 manufactured by BASF (compound name: 4-isobutylphenyl-4'-methylphenyliodonium hexafluorophosphate) or 2074 manufactured by Rhodia (compound name: 4-isopropylphenyl-4'-methylphenyliodonium tetrakispentafluorophenyl borate).

Among these onium salts, the iodonium salt may sometimes be inferior to the sulfonium salt in storage stability, and may have a problem such as discoloration during long-term storage. Accordingly, in a case where long-term storage stability is required, it is more preferred to use the sulfonium salt as the onium salt.

The above commonly used photoradical polymerization initiator is known to be susceptible to oxygen inhibition in radical polymerization and since the curing method of the present invention is conducted in the presence of oxygen, it is estimated to be susceptible to oxygen inhibition. However, the compound having a polycyclic aromatic skeleton of the present invention converts oxygen in the system to singlet oxygen which does not cause oxygen inhibition, and accordingly oxygen inhibition is reduced even in a system in which oxygen is present, and such a conventional photoradical polymerization initiator can function as a radical polymerization initiator.

EXAMPLES

Now, the present invention will be described in further detail with reference to Examples. However, Examples are merely exemplified as examples. That is, the following Examples are not exhaustive nor intended to restrict the present invention as described. Accordingly, the present invention is by no means restricted to the following Examples within a range not to exceed the scope of the present invention. Further, unless otherwise specified, all the parts and percentages are based on the weight.

The compounds of the present invention were identified using the following apparatus.

Infrared (IR) spectrophotometer: manufactured by Thermo Fisher Scientific, model iS50

FT-IR nuclear magnetic resonance ($^1$H-NMR) apparatus: manufactured by JEOL Ltd., model ECS-400

Preparation Example 1

Preparation of 9,10-bis(methoxycarbonylmethyleneoxy)anthracene

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 9.5 g (62.1 mmol) of methyl bromoacetate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, by suction filtration, 4.7 g (crude yield: 55 mol %) of yellow crystals were obtained.

(1) Melting point: 151-152° C.

(2) IR ($cm^{-1}$): 1745, 1391, 1363, 1164, 1093, 774, 705.

(3) $^1$H-NMR (400 MHz, $CDCl_3$): 5=3.914 (s, 6H), 4.792 (s, 4H), 7.261-7.545 (m, 4H), 8.319-8.366 (m, 4H).

Preparation Example 2

Preparation of 9,10-bis(ethoxycarbonylmethyleneoxy)anthracene

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 10.4 g (62.5 mmol) of ethyl bromoacetate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, by suction filtration, 5.0 g (crude yield: 55 mol %) of pale yellow crystals were obtained.

(1) Melting point: 93-94° C.

(2) IR ($cm^-$): 1754, 1742, 1382, 1367, 1241, 1212, 1168, 1087, 1034, 1004, 936, 809, 768, 720, 691, 669, 585.

(3) $^1$H-NMR (400 MHz, $CDCl_3$): δ=1.370 (t, J=14 Hz, 6H), 4.376 (k, J=21.6 Hz, 4H), 4.777 (s, 4H), 7.261-7.540 (m, 4H).

Preparation Example 3

Preparation of 9,10-bis(isopropoxycarbonylmethyleneoxy) anthracene

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 11.3 g (62.5 mmol) of isopropyl bromoacetate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, by suction filtration, 5.9 g (crude yield: 60 mol %) of pale yellow crystals were obtained.

(1) Melting point: 109-110° C.

(2) IR (cm$^{-1}$): 1744, 1360, 1210, 1163, 1086, 1018, 1004, 776, 768, 671.

(3) $^1$H-NMR (400 MHz, CDCl$_3$): δ=1.347 (d, J=6.4 Hz, 12H), 4.743 (s, 4H), 5.246-5.277 (m, 2H), 7.504-7.529 (m, 4H), 8.356-8.398 (m, 4H).

Preparation Example 4

Preparation of 9,10-bis(tert-butoxycarbonylmethyleneoxy) anthracene Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 12.2 g (62.5 mmol) of tert-butyl bromoacetate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, anthraquinone was removed by suction filtration, and the obtained filtrate was left to stand overnight to precipitate crystals. The crystals were collected by suction filtration to obtain 6.5 g (crude yield: 61 mol %) of pale yellow crystals.

(1) Melting point: 131-132° C.

(2) IR (cm$^{-1}$): 1742, 1391, 1358, 1232, 1151, 1089, 1021, 1004, 846, 776, 749, 670.

(3) $^1$H-NMR (400 MHz, CDCl$_3$): δ=1.575 (s, 18H), 4.659 (s, 4H), 7.260-7.530 (m, 4H), 8.359-8.400 (m, 4H).

Preparation Example 5

Preparation of 9,10-bis(n-butoxycarbonylmethyleneoxy)anthracene

Into a 100 ml four-necked flask equipped with a stirrer and a thermometer, in a nitrogen atmosphere, 15 g of methyl isobutyl ketone as a solvent, 3.1 g (4.8 mmol) of a 50% aqueous solution of tetrabutylammonium bromide as a catalyst, and 9.4 g (62.5 mmol) of butyl chloroacetate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, anthraquinone was removed by suction filtration, and the obtained filtrated was washed twice with water. After washing with water, anthraquinone precipitated, which was removed by suction filtration. The filtrate was left to stand overnight, and the precipitated crystals were collected by suction filtration to obtain 5.5 g (crude yield: 52 mol %) of yellow crystals.

(1) Melting point: 71-72° C.

(2) IR (cm$^{-1}$): 1749, 1411, 1385, 1364, 1246, 1226, 1167, 1085, 1035, 1018, 957, 768, 721, 669, 587.

(3) $^1$H-NMR (400 MHz, CDCl$_3$): δ=0.967 (d, J=15.2 Hz, 6H), 1.387-1.481 (m, 4H), 1.678-1.750 (m, 4H), 4.317 (t, J=13.2 Hz, 4H), 4.779 (s, 4H), 7.508-7.826 (m, 4H), 8.319-8.377 (m, 4H).

Preparation Example 6

Preparation of 9,10-bis(methoxycarbonylmethylmethyleneoxy)anthracene

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 10.4 g (62.5 mmol) of methyl 2-bromopropionate were added. While the temperature of the reaction system was kept at from 20 to 25° C., 29.1 g (24 mmol as anthraquinone) of a 17 wt % aqueous solution of 9,10-anthracenediol disodium salt was dropwise added over a period of at least 1 hour. After completion of the dropwise addition, the mixture was stirred further for 1 hour. Then, anthraquinone was removed by suction filtration, and the obtained filtrated was washed twice with water by liquid separation. The solution was concentrated by an evaporator, and the concentrate was cooled in a freezer to precipitate crystals, which were subjected to suction filtration to obtain 4.6 g (crude yield: 50 mol %) of yellow crystals.

(1) Melting point: 130-131° C.

(2) IR (cm$^{-1}$): 1737, 1366, 1207, 1134, 1078, 1061, 1020, 970, 748, 681.

(3) $^1$H-NMR (400 MHz, CDCl$_3$): δ=1.644 (d, J=6.4 Hz, 6H), 3.770 (s, 6H), 4.904 (k, J=20.4 Hz, 2H), 7.464-7.489 (m, 4H), 8.292-8.332 (m, 4H).

Preparation Example 7

Preparation of 9,10-bis(ethoxycarbonylpropyleneoxy)anthracene

Into a 100 ml four-necked flask equipped with a stirrer and a thermometer, in a nitrogen atmosphere, 0.77 g (1.19 mmol) of a 50% aqueous solution of tetrabutylammonium bromide as a catalyst, 12.1 g (61.8 mmol) of ethyl 4-bromoacetate, 5.0 g (23.8 mmol) of 9,10-anthracenediol, 9.9 g (71.4 mmol) of potassium carbonate, and 40 g of N,N-dimethylformamide as a solvent were added. While the temperature of the reaction system was kept at from 20 to 30° C., the mixture was stirred for one hour. Then, anthraquinone was removed by suction filtration, and the obtained filtrate was dissolved in toluene and washed twice with water. The solution was concentrated by an evaporator, and the concentrate was left to stand overnight, whereupon the entire solution was solidified. Methanol was added and the mixture was heated to 50° C. for dissolution. Undissolved anthraquinone was removed by suction filtration, and the filtrate was cooled in a freezer to precipitate crystals, which were subjected to suction filtration to obtain 5.4 g (crude yield: 51 mol %) of yellow crystals.

(1) Melting point: 95-96° C.

(2) IR (cm$^{-1}$): 1721, 1351, 1312, 1239, 1183, 1164, 1081, 1024, 1015, 913, 767, 742, 669.

(3) $^1$H-NMR (400 MHz, CDCl$_3$): δ=1.307 (t, J=14.0 Hz, 6H), 2.340-2.408 (m, 4H), 2.776 (t, J=14.8 Hz, 4H), 4.171-4.235 (m, 8H), 7.456-7.494 (m, 4H), 8.230-8.256 (m, 4H).

Preparation Example 8

Preparation of 9,10-bis(ethoxycarbonylbutyleneoxy)anthracene

Into a 100 ml four-necked flask equipped with a stirrer and a thermometer, in a nitrogen atmosphere, 0.77 g (1.19 mmol) of a 50% aqueous solution of tetrabutylammonium bromide as a catalyst, 12.9 g (61.8 mmol) of ethyl 5-bromovalerate, 5.0 g (23.8 mmol) of 9,10-anthracenediol, 9.9 g (71.4 mmol) of potassium carbonate and 40 g of N,N-dimethylformamide as a solvent were added. While the temperature of the reaction system was kept at from 20 to 30° C., the mixture was stirred for one hour. Then, anthraquinone was removed by suction filtration, and the obtained filtrate was dissolved in toluene and washed twice with water by liquid separation. The solution was concentrated by an evaporator. The concentrate was left to stand overnight, methanol was added to the concentrate, and undissolved anthraquinone was removed by suction filtration. The filtrate was cooled in a freezer to precipitate crystals, which were further subjected to suction filtration to obtain 6.2 g (crude yield: 55 mol %) of orange crystals.

(1) Melting point: 57-58° C.

(2) IR (cm$^{-1}$): 1722, 1403, 1337, 1284, 1269, 1229, 1178, 1167, 1068, 1021, 934, 763, 675.

(3) $^1$H-NMR (400 MHz, CDCl$_3$): δ=1.286 (t, J=14.4 Hz, 6H), 2.018-2.103 (m, 8H), 2.496 (t, J=13.6 Hz, 4H), 4.151-4.205 (m, 8H), 7.463-7.487 (m, 4H), 8.243-8.268 (m, 4H).

Preparation Example 9

Preparation of 2-ethyl-9,10-bis(isopropoxycarbonylmethyleneoxy)anthracene

Into a 200 ml four-necked flask equipped with a stirrer and a thermometer, in a nitrogen atmosphere, 5.0 g (21.2 mmol) of 2-ethylanthraquinone, 9.1 g (86.4 mmol) of thiourea dioxide, 8.4 g (211.6 mmol) of sodium hydroxide and 50 g of deionized water were added, followed by stirring while gradually heating to 120° C. Stirring was stopped when the solution become reddish black, and the solution was cooled at room temperature to prepare an aqueous solution of 2-ethyl-9,10-anthracenediol disodium salt. Then, into another 200 ml four-necked flask equipped with a stirrer and a thermometer, in a nitrogen atmosphere, 15 g of methyl isobutyl ketone as a solvent, 2.7 g (4.23 mmol) of a 50% aqueous solution of tetrabutylammonium bromide as a catalyst, and 10.0 g (55.0 mmol) of isopropyl bromoacetate were added. While the temperature of the reaction system was kept at from 20 to 25° C., the above prepared aqueous solution of 2-ethyl-9,10-anthracenediol disodium salt was dropwise added over a period of at least 1 hour. After completion of the dropwise addition, the mixture was stirred further for 1 hour. Then, the aqueous layer was removed, and the organic layer was concentrated by an evaporator to obtain 4.5 g (crude yield: 48 mol %) of an orange oil.

(1) Melting point: liquid at room temperature (2) IR (cm$^{-1}$): 1728, 1673, 1454, 1385, 1373, 1324, 1286, 1206, 1085, 962, 931, 901, 825, 772, 750, 712.

(3) $^1$H-NMR (400 MHz, CDCl$_3$): δ=1.237-1.371 (m, 15H), 2.816-2.899 (m, 2H), 4.731 (s, 4H), 5.014-5.123 (m, 1H), 5.225-5.301 (m, 1H), 7.391 (d, J=9.2 Hz, 1H), 7.461-7.512 (m, 2H), 7.766-7.790 (m, 1H), 8.119 (d, J=7.6 Hz, 1H), 8.284-8.368 (m, 2H).

<Photo DSC Measurement>

In this Example, photo DSC measurement was carried out as follows. That is, XDSC-7200 manufactured by Hitachi High-Technologies Corporation was used as a DSC measurement apparatus, and a photo DSC measurement unit was attached thereto so that DSC measurement could be conducted while applying light.

As a light source for light irradiation in polymerization reaction, LA-410UV manufactured by HAYASHI-REPIC CO., LTD. was used. As the light applied, light at a full wavelength by a high pressure mercury lamp or 405 nm light taken out by a band-pass filter was employed. The light illuminance was adjusted to be 100 mW/cm$^2$ at 365 nm in the case of light at a full wavelength by a high pressure mercury lamp or 50 mW/cm$^2$ in the case of 405 nm light. Light from the light source was led up to the upper part of the sample by glass fibers, and the shutter of the light source was trigger-controlled so that the DSC measurement could be started simultaneously with the start of light irradiation.

For photo DSC measurement, about 1 mg of a sample was accurately weighed in a measurement aluminum pan, which was put in a DSC measurement part, and the photo DSC unit was attached. In the DSC measurement part, nitrogen was made to flow at a rate of 100 mL/min, and measurement was conducted in a nitrogen atmosphere. After the first measurement, measurement was conducted again under the same conditions while the sample was as it was, and a value obtained by subtracting the second measurement result from the first measurement result was taken as the measurement result of the sample. The result was based on the total heating value per 1 mg of a sample, unless otherwise specified. As the polymerization reaction proceeds, heat generation occurs, and accordingly by measuring the total heating value, the degree of progress of the polymerization reaction can be examined.

Further, DSC measurement for thermal analysis was also conducted. About 1 mg of a sample was accurately weighed in a measurement aluminum sealing pan in a nitrogen atmosphere, which was put in a DSC measurement part. In the DSC measurement part, nitrogen was made to flow at a rate of 100 mL/min, and measurement was conducted in a nitrogen atmosphere. The result was based on the total heating value per 1 mg of a sample, unless otherwise specified. As the polymerization reaction proceeds, heat generation occurs, and accordingly by measuring the total heating value, the degree of progress of the polymerization reaction can be examined. Measurement was conducted at a temperature-raising rate of 5° C./min from 30° C. to 170° C.

Further, the degree of conversion was calculated based on the obtained total heating value of the exothermic peak obtained by enclosing trimethylolpropane triacrylate (TMPTA) (manufactured by Tokyo Chemical Industry Co., Ltd.) in an aluminum sealing pan and conducting thermal analysis at a temperature-raising rate of 5° C./min from 30° C. to 300° C. by DSC, being 100%.

<Measurement of Polymerization Behavior by Rheometer>

Whether the polymerization reaction proceeded or not can be confirmed by whether a viscosity increase was observed or not. This is to measure the change with time of the complex viscosity by a rheometer thereby to confirm progress of the polymerization reaction. As the rheometer, MCR102 manufactured by Anton Paar with option H-PTD200 to control the temperature and atmosphere, was used. Measurement was conducted using a parallel plate with a diameter of 10 mm, under conditions of strain: 100%, frequency: 1 Hz, temperature: constant at 25° C., measurement interval: 0.33 minute, gap: 0.5 mm. Further, in a case where the complex viscosity was measured using as the monomer trimethylolpropane triacrylate (TMPTA), it was judged that the polymerization proceeded at a point where the complex viscosity reached 10,000 Pa·s. The complex viscosity of trimethylolpropane triacrylate (TMPTA) as the monomer is usually from about 0.1 to about 0.6 Pa·s.

Example 1

Preparation of 9,10-dibutoxyanthracene-9,10-endoperoxide (DBAEPO, 9,10-dibutoxy-9,10-dihydro-9,10-epidioxyanthracene)

In a 50 ml Erlenmeyer flask, in the air, 226 mg (0.701 mmol) of 9,10-dibutoxyanthracene was dissolved in 7.5 ml of ethyl acetate (manufactured by Wako Pure Chemical Industries, Ltd., for spectroscopy). The solution was irradiated with light at a wavelength of 385 nm with an intensity of 122 mW/cm$^2$ from a LED lamp (manufactured by OPTOCODE CORPORATION, LED385/L-STND) for 2 hours and vacuum dried, and subjected to thin layer chromatography (silica gel, ethyl acetate: hexane=1:20, Rf value: 0.31) to obtain 144 mg (0.406 mmol) of 9,10-dibutoxyanthracene-9,10-endoperoxide as a colorless transparent liquid. The yield to the raw material 9,10-dibutoxyanthracene was 58.0 mol %.

(1) Melting point: 39-40° C.

(2) IR (liquid membrane method, cm$^{-1}$): 2957, 2872, 1461, 1298, 1073, 759.

(3) $^1$H-NMR (300 MHz, CDCl$_3$): δ=1.01 (t, J=7.3 Hz, 6H), 1.48-1.64 (m, 4H), 1.78-1.90 (m, 4H), 4.27 (t, J=6.6 Hz, 4H), 7.28 (dd, J=5.3 Hz, 3.0 Hz, 4H), 7.52 (dd, J=5.7 Hz, 3.4 Hz, 4H).

Example 2

Preparation of 9,10-bis(ethoxycarbonylmethyleneoxy)anthracene-9,10-endoperoxide (ECMAEPO)

In a 50 ml Erlenmeyer flask, in the air, 97.3 mg (0.254 mmol) of 9,10-bis(ethoxycarbonylmethyleneoxy)anthracene prepared in the same method as in Preparation Example 2 and 4.9 mg (7.6 mmol) of eosine Y as a singlet oxygen generator were dissolved in 10 ml of N,N-dimethylformamide (manufactured by Wako Pure Chemical Industries, Ltd., for spectroscopy). The solution was irradiated with light at a wavelength of 530 nm from a condensing LED light (manufactured by OPTOCODE CORPORATION, LED530/L-STND) for 3.5 hours from above the Erlenmeyer flask. Then, the solution was washed twice with ethyl acetate and washing water and once with ethyl acetate and pure water, the ethyl acetate layer was extracted, and sodium sulfate was added to remove water. The ethyl acetate layer was concentrated and vacuum dried and then subjected to thin layer chromatography (ethyl acetate:hexane=1:2, Rf value=0.7) to isolate 48.5 mg (0.117 mmol) of 9,10-bis (ethoxycarbonylmethyleneoxy)anthracene-9,10-endoperoxide as a colorless transparent liquid. The yield to the raw material 9,10-bis(ethoxycarbonylmethyleneoxy)anthracene was 46.1 mol %.

(1) Melting point: 80-81° C.

(2) IR (liquid membrane method, cm$^{-1}$): 2988, 2950, 1763, 1753, 1200, 1139, 1086, 1054, 902, 753.

(3) $^1$H-NMR (500 MHz, CDCl$_3$): δ=1.30-1.33 (t, J=7.3 Hz, 6H), 4.28-4.32 (q, J=7.0 Hz, 4H), 4.78 (s, 4H), 7.28-7.32 (dd, J=5.5 Hz, 3.0 Hz, 4H), 7.55-7.58 (dd, J=5.5 Hz, 3.5 Hz, 4H).

(4) $^{13}$C-NMR (125 MHz, CDCl$_3$): δ=14.3, 61.5, 64.0, 102.9, 120.6, 127.9, 137.9, 169.2.

Example 3

Photoradical Polymerization

To 100 parts by mass of trimethylolpropane triacrylate (TMPTA) (manufactured by Tokyo Chemical Industry Co., Ltd.) as a radical polymerizable compound, 1.5 parts by weight of 9,10-dibutoxyanthracene-9,10-endoperoxide (DBAEPO) obtained in the same manner as in Example 1 as a photoradical polymerization initiator was added to prepare a radical polymerizable composition. 1 mg of the radical polymerizable composition was accurately weighed in a measuring aluminum pan, which was set in a DSC measurement part, and a photo DSC unit was attached. The sample was irradiated with light at a full wavelength from a high pressure mercury lamp for 30 seconds. On that occasion, the heating value was 470 mJ/mg, and the degree of conversion was 83.9% (the results are shown in Table 1).

Comparative Example 1

The same operation as in Example 3 was conducted except that no 9,10-dibutoxyanthracene-9,10-endoperoxide (DBAEPO) as a photoradical polymerization initiator was added. On that occasion, the heating value was 26.3 mJ/mg, and the degree of conversion was 7.4% (the results are shown in Table 1).

Example 4

Heat Radical Polymerization

To 100 parts by weight of trimethylolpropane triacrylate (TMPTA) (manufactured by Tokyo Chemical Industry Co., Ltd.) as a radical polymerizable compound, 1.5 parts by weight of 9,10-dibutoxyanthracene-9,10-endoperoxide (DBAEPO) obtained in the same manner as in Example 1 as a heat radical polymerization initiator was added to prepare a radical polymerizable composition. 1 mg of the radical polymerizable composition was accurately weighed in a measurement aluminum sealing pan in a nitrogen atmosphere, which was set to a DSC measurement part, and measurement was conducted at a temperature-raising rate of 5° C./min from 30° C. to 170° C. On that occasion, the heating value was 503 mJ/mg, and the degree of conversion was 88.2% (the results are shown in Table 1).

Comparative Example 2

The same operation as in Example 4 was conducted except that no 9,10-dibutoxyanthracene-9,10-endoperoxide (DBAEPO) as a heat radical polymerization initiator was added. On that occasion, the heating value was 0 mJ/mg, and the degree of conversion was 0.0% (the results are shown in Table 1).

Example 5

The same operation as in Example 3 was conducted except that 1.5 parts of 9,10-bis(ethoxycarbonylmethyleneoxy)anthracene-9,10-endoperoxide (ECMAEPO) prepared in the same manner as in Example 2 was added instead of 1.5 parts of 9,10-dibutoxyanthracene-9,10-endoperoxide (DBAEPO) in Example 3. On that occasion, the heating value was 284 mJ/mg, and the degree of conversion was 49.8% (the results are shown in Table 1).

TABLE 1

|  | Radical polymerization initiator | | Irradiation energy | Total heating value (mg/mJ) | Degree of conversion (%) |
|---|---|---|---|---|---|
|  | Initiation species | Amount added (parts by weight) |  |  |  |
| Example 3 | DBAEPO | 1.5 | UV | 470 | 83.9 |
| Example 4 |  | 1.5 | Heat | 503 | 88.2 |
| Example 5 | ECMAEPO | 1.5 | UV | 284 | 49.8 |
| Comparative Example 1 | Nil | — | UV | 26.3 | 7.4 |
| Comparative Example 2 |  |  | Heat | 0.0 | 0.0 |

*DBAEPO: 9,10-dibutoxyanthracene-9,10-endoperoxide
*ECMAEPO: 9,10-bis(ethoxycarbonylmethyleneoxy)anthracene-9,10-endoperoxide Example 6

To 100 parts by weight of trimethylolpropane triacrylate (TMPTA) (manufactured by Tokyo Chemical Industry Co., Ltd.) as a radical polymerizable compound, 5 parts by weight of a cobalt naphthenate mineral sprit solution (Co: 6%) (manufactured by Wako Pure Chemical Industries, Ltd.) as a reducing agent to promote deposition of the endoperoxide was added. The solution in an amount to be sandwiched between parallel plates with a diameter of 10 mm with a gap of 0.5 mm, was placed on a heat plate kept at 25° C. of a rheometer. On this solution, a very small amount (about 50 mg) of 9,10-dibutoxyanthracene-9,10-endoperoxide (DBAEPO) obtained in the same manner as in Example 1 as a heat radical polymerization initiator was put, and immediately the solution was sandwiched between the parallel plates and measurement of the complex viscosity was started by the rheometer. As a result, about 20 minutes after start of the measurement, a complex viscosity increase was observed, and 61 minutes after start of the measurement, the complex viscosity reached 10,080 Pa·s, and reached 44,260 Pa·s 90 minutes after start of the measurement. This proves that the polymerization reaction proceeded in this solution (the results are shown in Table 2).

Comparative Example 3

The same operation as in Example 6 was conducted except that no 9,10-dibutoxyanthracene-9,10-endoperoxide (DBAEPO) as a heat radical polymerization initiator was added. As a result, substantially no complex viscosity increase was observed even 90 minutes after start of the measurement, and the viscosity 90 minutes after start of the measurement was 0.3 Pas. This proves that no polymerization reaction proceeded in this solution (the results are shown in Table 2).

Example 7

To 100 parts by weight of trimethylolpropane triacrylate (TMPTA) (manufactured by Tokyo Chemical Industry Co., Ltd.) as a radical polymerizable compound, 1.5 parts by weight of 9,10-dibutoxyanthracene-9,10-endoperoxide (DBAEPO) obtained in the same manner as in Example 1 as a photoradical polymerization initiator was added and further, 0.01 part by weight of DBA (9,10-dibutoxyanthracene) as a photoradical polymerization sensitizer was added to prepare a radical polymerizable composition. 1 mg of the radical polymerizable composition was accurately weighed in a measurement aluminum pan, which was set to a DSC measurement part, and a photo DSC unit was attached. The sample was irradiated with 405 nm light for 2 minutes in a nitrogen atmosphere. On that occasion, the heating value was 266 mJ/mg, and the degree of conversion was 53.2% (the results are shown in Table 3).

Example 8

To 100 parts by weight of trimethylolpropane triacrylate (TMPTA) (manufactured by Tokyo Chemical Industry Co., Ltd.) as a radical polymerizable compound, 1.5 parts by weight of 9,10-dibutoxyanthracene-9,10-endoperoxide (DBAEPO) obtained in the same manner as in Example 1 as a photoradical polymerization initiator was added, and further 0.5 part by weight of OcA(9,10-bis(octanoyloxy)anthracene) as a photoradical polymerization sensitizer was added to prepare a radical polymerizable composition. 1 mg of the radical polymerizable composition was accurately weighed in a measurement aluminum pan, which was set to a DSC measurement part, and a phot DSC unit was attached. The sample was irradiated with 405 nm light for 5 minutes in a nitrogen atmosphere. On that occasion, the heating value was 359 mJ/mg, and the degree of conversion was 71.8% (the results are shown in Table 3).

TABLE 2

|  | Heat radical polymerization initiator | Decomposition promotor | Complex viscosity immediately after start of measurement (Pa/s) | Complex viscosity 90 minutes after start of measurement (Pa/s) | Polymerization reaction |
|---|---|---|---|---|---|
| Example 6 | DBAEPO | Used | 0.1 | 44,260 | Proceeded |
| Comparative Example 3 | Nil | Used | 0.1 | 0.3 | Not proceeded |

*DBAEPO: 9,10-dibutoxyanthracene-9,10-endoperoxide

Example 9

To 100 parts by weight of trimethylolpropane triacrylate (TMPTA) (manufactured by Tokyo Chemical Industry Co., Ltd.) as a radical polymerizable compound, 1.5 parts by weight of 9,10-dibutoxyanthracene-9,10-endoperoxide (DBAEPO) obtained in the same manner as in Example 1 as a photoradical polymerization initiator was added, and further, 0.5 part by weight of ECMA (9,10-bis(ethoxycarbonylmethyleneoxy)anthracene) prepared in the same manner as in Preparation Example 2 as a photoradical polymerization sensitizer was added to prepare a radical polymerizable composition. 1 mg of the radical polymerizable composition was accurately weighed in a measurement aluminum pan, which was set to a DSC measurement part, and a photo DSC unit was attached. The sample was irradiated with 405 nm light for 5 minutes in a nitrogen atmosphere. On that occasion, the heating value was 400 mJ/mg, and the degree of conversion was 70.1% (the results are shown in Table 3).

TABLE 3

| | Photoradical polymerization initiator | | Photoradical polymerization sensitizer | | Wavelength of light applied (nm) | Total heating value (mg/mJ) | Degree of conversion (%) |
|---|---|---|---|---|---|---|---|
| | Initiation species | Amount added (parts by weight) | Sensitizer species | Amount added (parts by weight) | | | |
| Example 7 | DBAEPO | 1.5 | DBA | 0.01 | 405 | 266 | 53.2 |
| Example 8 | | | OcA | 0.5 | | 359 | 71.8 |
| Example 9 | | | ECMA | 0.5 | | 400 | 70.1 |

*DBAEPO: 9,10-dibutoxyanthracene-9,10-endoperoxide
DBA: 9,10-dibutoxyanthracene
OcA: 9,10-bis(octanoyloxy)anthracene
ECMA: 9,10-bis(ethoxycarbonylmethyleneoxy)anthracene As evident from comparison between Examples 3 and 5 and Comparative Example 1, 9,10-dibutoxyanthracene-9,10-endoperoxide (DBAEPO) and 9,10-bis(ethoxycarbonylmethyleneoxy)anthracene-9,10-endoperoxide (ECMAEPO) form an initiation radical to initiate radical polymerization by irradiation with ultraviolet rays.

Further, as evident from comparison between Example 4 and Comparative Example 2, 9,10-dibutoxyanthracene-9,10-endoperoxide (DBAEPO) forms an initiation radical to initiate radical polymerization also by applying a heat energy.

As evident from comparison between Example 6 and Comparative Example 3, 9,10-dibutoxyanthracene-9,10-endoperoxide (DBAEPO) does not decompose at 25° C. and does not function as a radical polymerization initiator, however, even at 25° C., by adding cobalt naphthenate as a decomposition promoter, a Redox reaction occurs, and the endoperoxide forms an initiation radical to initiate radical polymerization, whereby radical polymerization proceeds.

The following is evident from Examples 7, 8 and 9. That is, as shown in FIG. 1, 9,10-dibutoxyanthracene-9,10-endoperoxide (DBAEPO) has no absorption in a wavelength region of at least 330 nm. Thus, it does not undergo decomposition reaction by irradiation with 405 nm light employed in the above Examples, and thus does not undergo a polymerization reaction. However, by adding the compound having a polycyclic aromatic skeleton (DBA, OcA, ECMA) having absorption at 405 nm of the present invention as a photoradical polymerization sensitizer, the anthracene compound is excited by 405 nm light, and the energy is transferred to DBAEPO, whereby DBAEPO is decomposed to form an initiation radical to initiate radical polymerization.

INDUSTRIAL APPLICABILITY

The present invention is to provide a novel radical polymerization method in which in a polymerization reaction of a radical polymerizable compound, oxygen which causes oxygen inhibition is positively utilized to produce an endoperoxide compound having a polycyclic aromatic skeleton from a compound having a polycyclic aromatic skeleton, and the endoperoxide compound having a polycyclic aromatic skeleton is used as a radical polymerization initiator, and further provides a novel radical polymerizable composition using the compound having a polycyclic aromatic skeleton of the present invention and its polymerization method, and to provide an industrially highly useful radical polymerizable composition.

The invention claimed is:

1. An endoperoxide compound of formula (1):

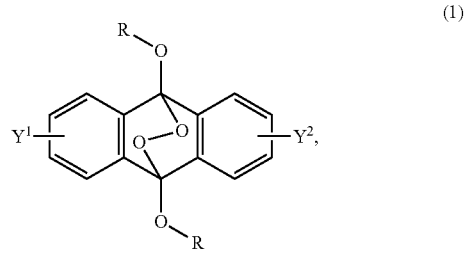

wherein

R is an alkoxymethyl group comprising a $C_{1-5}$ alkoxy group, an alkyloxycarbonylmethyl group comprising a $C_{1-12}$ alkyl group, or an aryloxycarbonylmethyl group comprising a $C_{6-12}$ aryl group, and $Y^1$ and $Y^2$ are independently H, a $C_{1-8}$ alkyl group, or a halogen atom.

2. The compound of claim 1, which has a formula (5):

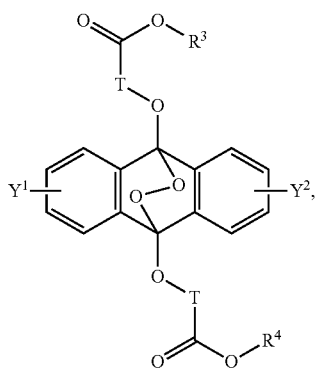

wherein
T is a $C_{1-20}$ alkylene group, optionally branched by an alkyl group,
each of $R^3$ and $R^4$ is a $C_{1-20}$ alkyl group, and
each of $Y^1$ and $Y^2$ is a hydrogen atom, a $C_{1-8}$ alkyl group, or a halogen atom.

3. A photoradical polymerization initiator comprising an endoperoxide compound of formula (1):

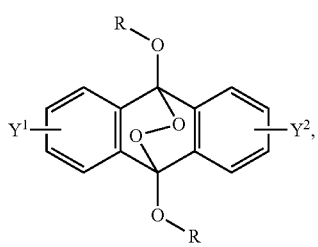

wherein
R is an alkoxymethyl group comprising a $C_{1-5}$ alkoxy group an alkyloxycarbonylmethyl group comprising a $C_{1-12}$ alkyl group, or an aryloxycarbonylmethyl group comprising a $C_{6-12}$ aryl group, and
each of $Y^1$ and $Y^2$ is H, a $C_{1-8}$ alkyl group, or a halogen atom.

4. A heat radical polymerization initiator, comprising:
an endoperoxide compound of formula (1):

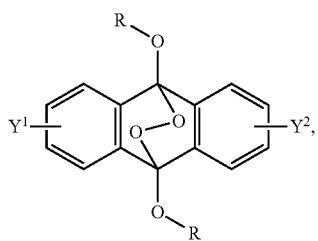

wherein
R is an alkoxymethyl group comprising a $C_{1-5}$ alkoxy group, an alkyloxycarbonylmethyl group comprising a $C_{1-12}$ alkyl group, or an aryloxycarbonylmethyl group comprising a $C_{6-12}$ aryl group, and
each of $Y^1$ and $Y^2$ is H, a $C_{1-8}$ alkyl group, or a halogen atom.

5. A radical polymerizable composition, comprising:
the photoradical polymerization initiator of claim 3; and
a radical polymerizable compound.

6. A radical polymerizable composition, comprising:
the heat radical polymerization initiator of claim 4; and
a radical polymerizable compound.

7. The composition of claim 5, further comprising:
a photoradical polymerization sensitizer.

8. The composition of claim 6, further comprising:
a decomposition promoter for the heat radical polymerization initiator.

9. A method for curing a radical polymerizable composition, the method comprising:
irradiating a radical polymerizable composition comprising a compound of formula (2):

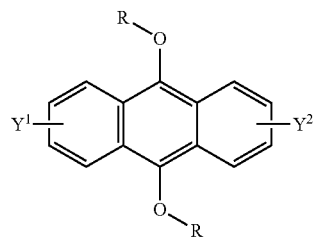

R being an alkoxymethyl group comprising a $C_{1-5}$ alkoxy group, an alkyloxycarbonylmethyl group comprising a $C_{1-12}$ alkyl group, or an aryloxycarbonylmethyl group comprising a $C_{6-12}$ aryl group, and $Y^1$ and $Y^2$ each being H, a $C_{1-8}$ alkyl group, or a halogen atom; and a radical polymerizable compound, with ultraviolet rays in the presence of oxygen to produce an endoperoxide compound of formula (1):

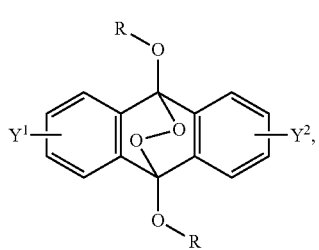

R being an alkoxymethyl group comprising a $C_{1-5}$ alkoxy group an alkyloxycarbonylmethyl group comprising a $C_{1-12}$ alkyl group, or an aryloxycarbonylmethyl group comprising a $C_{6-12}$ aryl group, and $Y^1$ and $Y^2$ each being, a $C_{1-8}$ alkyl group, or a halogen atom; and
conducting a polymerization reaction using the endoperoxide compound as a photoradical polymerization initiator and/or a heat radical polymerization initiator.

10. The method of claim 9, wherein the compound of formula (2) has a formula (4):

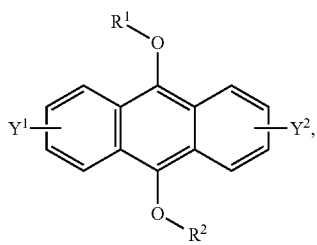
(4)

each of $R^1$ and $R^2$ being an alkoxymethyl group comprising a $C_{1-5}$ alkoxy group, an alkyloxycarbonyl group comprising a $C_{1-10}$ alkyl group, or an aryloxycarbonyl group comprising a $C_{6-10}$ aryl group, and each of $Y^1$ and $Y^2$ being H, a $C_{1-8}$ alkyl group or a halogen atom, and wherein the endoperoxide compound has formula (3):

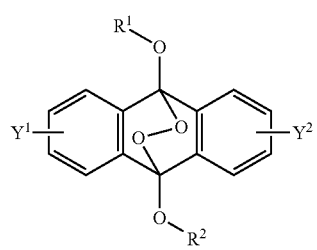
(3)

each of $R^1$ and $R^2$ being an alkoxymethyl group comprising a $C_{1-5}$ alkoxy group, an alkyloxycarbonyl group comprising a $C_{1-10}$ alkyl group, or an aryloxycarbonyl group comprising a $C_{6-10}$ aryl group, and each of $Y^1$ and $Y^2$ being H, a $C_{1-8}$ alkyl group, or a halogen atom.

11. The method of claim 9, wherein the compound of formula (2) has a formula (6):

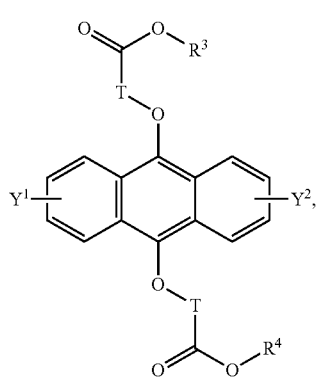
(6)

T being a $C_{1-20}$ alkylene group, optionally branched by an alkyl group, each of $R^3$ and $R^4$ being a $C_{1-20}$ alkyl group, and each of $Y^1$ and $Y^2$ being H, a $C_{1-8}$ alkyl group, or a halogen atom, and wherein the endoperoxide compound has formula (5):

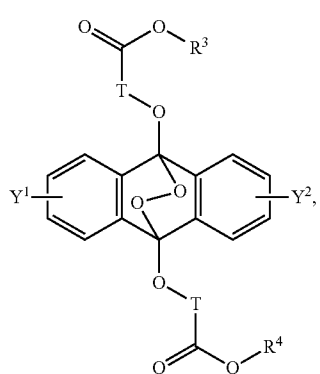
(5)

T being a $C_{1-20}$ alkylene group, optionally branched by an alkyl group, each of $R^3$ and $R^4$ being a $C_{1-20}$ alkyl group, and each of $Y^1$ and $Y^2$ being H, a $C_{1-8}$ alkyl group, or a halogen atom.

* * * * *